US011560387B2

(12) United States Patent
Trant et al.

(10) Patent No.: US 11,560,387 B2
(45) Date of Patent: Jan. 24, 2023

(54) THERMALLY SENSITIVE PROTECTING GROUPS FOR CYSTEINE, AND MANUFACTURE AND USE THEREOF

(71) Applicant: University of Windsor, Windsor (CA)

(72) Inventors: John Frederick Trant, LaSalle (CA); Daniel Meister, Windsor (CA); Sarah Nasri, LaSalle (CA); Anthony Emanuel Chifor, LaSalle (CA); John James Hayward, Windsor (CA); Seyedeh Maryamdokht Taimoory, LaSalle (CA); Mohadeseh Dashti-Pour, Windsor (CA)

( * ) Notice: Subject to any disclaimer, the term of this patent is extended or adjusted under 35 U.S.C. 154(b) by 0 days.

(21) Appl. No.: 17/468,048

(22) Filed: Sep. 7, 2021

(65) Prior Publication Data
US 2022/0024942 A1 Jan. 27, 2022

Related U.S. Application Data

(63) Continuation of application No. 16/985,815, filed on Aug. 5, 2020, now abandoned.

(60) Provisional application No. 62/883,332, filed on Aug. 6, 2019.

(51) Int. Cl.
*C07D 491/18* (2006.01)
*C07K 1/06* (2006.01)

(52) U.S. Cl.
CPC ............ *C07D 491/18* (2013.01); *C07K 1/067* (2013.01)

(58) Field of Classification Search
None
See application file for complete search history.

(56) References Cited

PUBLICATIONS

Stevenson, F., Jr., Cysteine and Selenocysteine Deprotection Chemistry in Peptide Synthesis. Mini-Reviews in Organic Chemistry 2009, 6 (3), 196-210.
Ramos-Tomillero, I.; Mendive-Tapia, L.; Góngora-Benítez, M.; Nicolás, E.; TullaPuche, J.; Albericio, F., Understanding Acid Lability of Cysteine Protecting Groups. Molecules 2013, 18 (5), 5155.
Hibino, H.; Miki, Y.; Nishiuchi, Y., Evaluation of acid-labile S-protecting groups to prevent Cys racemization in Fmoc solid-phase peptide synthesis. Journal of Peptide Science 2014, 20 (1), 30-35.
Harris, K. M.; Flemer, S.; Hondal, R. J., Studies on deprotection of cysteine and selenocysteine side-chain protecting groups. Journal of Peptide Science 2007, 13 (2), 81-93.
Góngora-Benítez, M.; Mendive-Tapia, L.; Ramos-Tomillero, I.; Breman, A. C.; Tulla-Puche, J.; Albericio, F., Acid-Labile Cys-Protecting Groups for the Fmoc/tBu Strategy: Filling the Gap. Organic Letters 2012, 14 (21), 5472-5475.
Kondasinghe, T. D.; Saraha, H. Y.; Odeesho, S. B.; Stockdill, J. L., Direct palladium-mediated on-resin disulfide formation from Allocam protected peptides. Organic & Biomolecular Chemistry 2017, 15 (14), 2914-2918.
Kotzur, N.; Briand, B.; Beyermann, M.; Hagen, V., Wavelength-Selective Photoactivatable Protecting Groups for Thiols. Journal of the American Chemical Society 2009, 131 (46), 16927-16931.
Shen, F.; Zhang, Z.-P.; Li, J.-B.; Lin, Y.; Liu, L., Hydrazine-Sensitive Thiol Protecting Group for Peptide and Protein Chemistry. Organic Letters 2011,13 (4), 568-571.
Postma, T. M.; Giraud, M.; Albericio, F., Trimethoxyphenylthio as a Highly Labile Replacement for tert-Butylthio Cysteine Protection in Fmoc Solid Phase Synthesis. Organic Letters 2012, 14 (21), 5468-5471.
Hibino, H.; Nishiuchi, Y., 4-Methoxybenzyloxymethyl Group, a Racemization Resistant Protecting Group for Cysteine in Fmoc Solid Phase Peptide Synthesis. Organic Letters 2012, 14 (7), 1926-1929.
Muttenthaler, M.; Ramos, Y. G.; Feytens, D.; Araujo, A. D. d.; Alewood, P. F., pNitrobenzyl protection for cysteine and selenocysteine: A more stable alternative to the acetamidomethyl group. Peptide Science 2010, 94 (4), 423-432.
Katayama, H.; Nakahara, Y.; Hojo, H., N-Methyl-phenacyloxycarbamidomethyl (Pocam) group: a novel thiol protecting group for solid-phase peptide synthesis and peptide condensation reactions. Organic & Biomolecular Chemistry 2011, 9(12), 4653-4661.
Grajkowski, A.; Cieslak, J.; Gapeev, A.; Beaucage, S. L., Hydroxyalkylated phosphoramidate, phosphoramidothioate and phosphorodiamidothioate derivatives as thiophosphate protecting groups in the development of thermolytic DNA prodrugs. New Journal of Chemistry 2010, 34 (5), 880-887.
Chmielewski, M. K.; Marchán, V.; Cieślak, J.; Grajkowski, A.; Livengood, V.; Münch, U.; Wilk, A.; Beaucage, S. L., Thermolytic Carbonates for Potential 5'-Hydroxyl Protection of Deoxyribonucleosides. The Journal of Organic Chemistry 2003, 68 (26), 10003-10012.
Cole, K. P.; Ryan, S. J.; Groh, J. M.; Miller, R. D., Reagent-free continuous thermal tert-butyl ester deprotection. Bioorgan. Med. Chem. 2017, 25 (23), 6209- 6217.
Miyake, H.; Tsumura, T.; Sasaki, M., Simple deprotection of acetal type protecting groups under neutral conditions. Tetrahedron Letters 2004, 45 (39), 7213-7215.
Peterson, G. I.; Church, D. C.; Yakelis, N. A.; Boydston, A. J., 1,2-oxazine linker as athermal trigger for self-immolative polymers. Polymer 2014, 55 (23), 5980-5985.
Fan, B.; Trant, J. F.; Hemery, G.; Sandre, O.; Gillies, E. R., Thermo-responsive self-immolative nanoassemblies: Direct and indirect triggering. Chem. Commun. 2017, 12068-12071.
Taimoory, S. M.; Sadraei, S. I.; Fayoumi, R.; Nasri, S.; Revington, M.; Trant, J.F., Preparation and Characterization of a Small Library of Thermally-Labile End-Caps for Variable-Temperature Triggering of Self-immolative Polymers. J. Org. Chem. 2018, 83.8 (2018): 4427-4440.

(Continued)

*Primary Examiner* — Samantha L Shterengarts

(57) ABSTRACT

In a preferred embodiment, there is provided a protecting group for protecting the thiol side chain of a cysteine residue, the protecting group comprising a Diels-Alder cycloadduct of a furan and a maleimide, and optionally, a linker interposed between the thiol side chain and the Diels-Alder cycloadduct.

7 Claims, 2 Drawing Sheets

(56) References Cited

PUBLICATIONS

DeWit, M. A.; Gillies, E. R., A cascade biodegradable polymer based on alternating cyclization and elimination reactions. J. Am. Chem. Soc. 2009, 131 (51), 18327-18334.
DeWit, M. A.; Gillies, E. R., Design, synthesis, and cyclization of 4-aminobutyric acid derivatives: potential candidates as self-immolative spacers. Org. Biomol. Chem. 2011, 9 (6), 1846-1854.
McBride, R. A.; Gillies, E. R., Kinetics of self-immolative degradation in a linear polymeric system: demonstrating the effect of chain length. Macromolecules 2013, 46 (13), 5157-5166.
J. H. Kamps, T. Hoeks, E. Kung, J. P. Lens, P. J. McCloskey, B. A. J. Noordover and J. P. A. Heuts, Activated carbonates: enabling the synthesis of differentiated polycarbonate resins via melt transcarbonation, Polym. Chem., 2016, 7, 5294-5303.
Maximiliano Sortino, Valdir Cechinel Filho, Rogério Corrêa, Susana Zacchino, N-Phenyl and N-phenylalkyl-maleimides acting against *Candida* spp.: Time-to-kill, stability, intera.
Sortino, M. et al., Antifungal, cytotoxic and SAR studies of a series of N-alkyl, N-aryl and N-alkylphenyl-1,4-pyrrolediones and related compounds. Bioorgan. Med. Chem. 2011, 19 (9), 2823-2834. DOI: http://dx.doi.org/10.1016/j.bmc. 2011.03.038.
Lee, H. S. et al., Substituent chemical shifts of N-arylsuccinanilic acids, N-arylsuccinimides, N-arylmaleanilic acids, and N-arylmaleimides. Magn. Reson. Chem. 2009, 47 (9), 711-715. DOI: 10.1002/mrc.2450.
Jim H. et al., Pestic. Biochem. Physiol. 2009, 93 (3), 133-137. DOI: https://doi.org/10.1016/j.pestbp.2009.01.002.
Natarajan, P. et al., Silver(I)-Promoted ipso-Nitration of Carboxylic Acids by Nitronium Tetrafluoroborate. J. Org. Chem. 2015, 80 (21), 10498-10504. DOI: 10.1021/acs.joc.5b02133.
Emami, S. et al., 7-Piperazinylquinolones with methylene-bridged nitrofuran scaffold as new antibacterial agents. Med. Chem. Res. 2013, 22 (12), 5940-5947. DOI: 10.1007/s00044-013-0581-9.
Berry, J. M. et al., 5-Nitrofuran-2-ylmethyl group as a potential bioreductively activated pro-drug system. J. Chem. Soc. Perkin. Trans. 1 1997, (8), 1147-1156. DOI: 10.1039/a607202j.
Torii, S. et al., Anodic Reaction of 2-Furoic Acids. II. Electrolysis of Methyl 5-Acetyl-2-furoate and Its Homologous in Protic Solvents. Bull. Chem. Soc. Jpn. 1972, 45 (9), 2783-2787. DOI: 10.1246/bcsj.45.2783.
Bi, J. et al., Application of furyl-stabilized sulfur ylides to a concise synthesis of 8a-epi-swainsonine. Chem. Commun. 2008, (1), 120-122. DOI: 10.1039/b713447a.
Fieser, L. F. et al., Reagents for Organic Synthesis. Wiley: New York, 1976; p. 1140.
Amundsen, L. H. et al., Reduction of Nitriles to Primary Amines with Lithium Aluminum Hydridel. J. Am. Chem. Soc. 1951, 73 (1), 242-244. DOI: 10.1021/ja01145a082.
Schwartz, D. A. et al., Synthetic approaches to haplophytine. 2. Synthesis of 4-methylamino-1-(2-furanyl)-2-phenyl-2-(2-pivaloylamidophenyl)butan-1-one. Can. J. Chem. 1983, 61 (6), 1126-1131. DOI: 10.1139/v83-201.
Manly, D. G. et al., Simple Furan Ethers. II: 2-Alkoxy- and 2-Aryloxy-furans. J. Org. Chem. 1956, 21 (5), 516-519. DOI: 10.1021 /jo01111 a008.
Chan, W. C. et al., Basic procedures. In Fmoc Solid Phase Peptide Synthesis: A Practical Approach, Chan, W. C.; White, P. D., Eds. Oxford University Press: Oxford, 2000; pp. 41-76.
Kurti, L.; Czako, B. Diels—Alder Cycloaddition. In Strategic Application of Named Reactions in Organic Synthesis; Elsevier: Burlington, MA, 2005; p. 140.
Nicolaou, K. C.; Snyder, S.A.; Montagnon, T.; Vassilikogiannakis, G. Angew. Chem. Int. Ed. 2002, 41, 1668.
Kolb, H.C.; Finn, M.G.; Sharpless, K.B. Angew. Chem. Int. Ed. 2001, 40, 2004.
Kotha, S.; Banerjee; S. RSC Adv. 2013, 3, 7642.
Gangini, A. Prog. Polym. Sci. 2013, 38, 1.
Liu, Y.L.; Chuo, T.W. Polym. Chem. 2013, 4, 2194.
Becker, G.; Marquetant, T. A.; Wagner, M.; Wurm, F. R. Macromolecules 2017, 50, 7852.
Cengriz, N.; Gevrek, T. N.; Sanyal, R.; A. Chem. Commun. 2017, 53, 8894.
Chujo, Y.; Sada, K.; Saegusa, T.; Macromolecules 1990, 23, 2636.
Nimmo, C. M.; Owen, S. C.; Shoichet, M. S. Biomacromolecules 2011, 12, 824.
Smith, L.; Taimoory, S. M.; Tam, R. Y.; Baker, A. E. G.; Binth Mohammad, N.; Trant, J. F.; Shoichet, M. S. Biomacromolecules 2018, 19, 926.
Bai, X.; Lu; S.; Cao, Z.; Ni, B.; Wang, X.; Ning, P.; Ma, D.; Wei, H.; Liu, M. Carbohydr. Polym. 2017, 166, 123.
Liu, G.; Zhang, G.; Hu, J.; Wang, X.; Zhu, M.; Liu, S. J. Am. Chem. Soc. 2015, 137, 11645.
Liu, G.; Wang, X.; Hu, J.; Zhang, G.; Liu, S. J. Am. Chem. Soc. 2014, 136, 7492.
Fan, B.; Trant, J. F.; Gillies, E. R. Macromolecules 2016, 49, 9309.
Fan, B.; Trant, J. F.; Yardley, R. E.; Pickering, A. J.; Lagugne-Labarthet, F.; Gillies, E. R. Macromolecules 2016, 49, 7196.
Dou, Y.; Hynynen, K.; Allen, C. J. Controlled Release 2017, 249, 63.
Toraya-Brown, S.; Fiering, S. Int. J. Hyperthermia 2014, 30, 531.
Zanetti, J. E.; Bashour, J. T. J. Am. Chem. Soc. 1939, 61, 2249.
Fan, B.; Trant, J.; Wong, A. D.; Gillies, E. R. J. Am. Chem. Soc. 2014, 136, 10116.
Fleming, I. Thermal Pericyclic Reactions. In Molecular Orbitals and Organic Chemical Reactions; John Wiley & Sons, Ltd: Chichester: United Kingdom, 2010; p. 253.
Higson, S.; Subrizi, F.; Sheppard, T. D.; Hailes, H. C. Green Chem. 2016, 18, 1855.
Celia, I. A. J. Org. Chem. 1988, 53, 2099.
Li, J.-L.; Yue, C.-Z.; Chen, P.-Q.; Xiao, Y.-C.; Chen, Y.-C. Angew. Chem., Int. Ed. 2014, 53, 5449.
Woodward, R. B.; Katz, T. J. Tetrahedron 1959, 5, 70.
Jasinski, R. J. Mol. Graphics Modell. 2017, 75, 55.
Bauld, N. L.; Yang, J. Tetrahedron Lett. 1999, 40, 8519.
Harvey, R. S.; Mackay, E. G.; Roger, L.; Paddon-Row, M. N.; Sherburn, M. S.; Lawrence, A. L. Angew. Chem., Int. Ed. 2015, 54, 1795.
Linder, M.; Brinck, T. Phys. Chem. Chem. Phys. 2013, 15, 5108.
Tang, S.-Y.; Shi, J.; Guo, Q.-X. Org. Biomol. Chem. 2012, 10, 2673.
Rivero, U.; Meuwly, M.; Willitsch, S. Chem. Phys. Lett. 2017, 683, 598.
Frisch, M. J., et al.Gaussian 09; Gaussian, Inc.: Wallingford, CT, 2009.
Becke, A. D. Phys. Rev. A: At., Mol., Opt. Phys. 1988, 38, 3098.
Lee, C.; Yang, W.; Parr, R. G. Phys. Rev. B: Condens. Matter Mater. Phys. 1988, 37, 785.
Duan, A.; Yu, P.; Liu, F.; Qiu, H.; Gu, F. L.; Doyle, M. P.; Houk, K. N. J. Am. Chem. Soc. 2017, 139, 2766.
Levandowski, B. J.; Houk, K. N. J. Org. Chem. 2015, 80, 3530.
Tomasi, J.; Mennucci, B.; Cances, E. J. Mol. Struct.: THEOCHEM 1999, 464, 211.
Sheldrick, G. Acta Crystallogr., Sect. C: Struct. Chem. 2015, 71, 3.
S. Ganta, H. Devalapally, A. Shahiwala and M. Amiji, J. Controlled Release, 2008, 126, 187.
J. Ge, T. Huynh, Y. Hu and Y. Yin, Nano Lett., 2008, 8, 931.
Y. Wang, A. S. Angelatos and F. Caruso, Chem. Mater., 2007, 20, 848.
J. Zhuang, M. R. Gordon, J. Ventura, L. Li and S. Thayumanavan, Chem. Soc. Rev., 2013, 42, 7421.
J. S. Katz and J. A. Burdick, Macromol. Biosci., 2010, 10, 339.
W. Agut, A. Brulet, C. Schatz, D. Taton and S. Lecommandoux, Langmuir, 2010, 26, 10546.
J. Liu, Y. Huang, A. Kumar, A. Tan, S. Jin, A. Mozhi and X. J. Liang, Biotechnol. Adv., 2014, 32, 693.
X. Huang, I. H. El-Sayed, W. Qian and M. A. El-Sayed, J. Am. Chem. Soc., 2006, 128, 2115.
G. Hemery, E. Garanger, S. Lecommandoux, A. D. Wong,E. R. Gillies, B. Pedrono, T. Bayle, D. Jacob and O. Sandre, J. Phys. D: Appl. Phys., 2015, 48, 494001.
S. Qin, Y. Geng, D. E. Discher and S. Yang, Adv. Mater., 2006, 18, 2905.

(56) References Cited

PUBLICATIONS

A. W. Jackson and D. A. Fulton, Polym. Chem., 2013, 4, 31.
M. E. Roth, O. Green, S. Gnaim and D. Shabat, Chem. Rev., 2015, 116, 1309.
A. Sagi, R. Weinstain, N. Karton and D. Shabat, J. Am. Chem. Soc., 2008, 130, 5434.
M. G. Olah, J. S. Robbins, M. S. Baker and S. T. Phillips, Macro-molecules, 2013, 46, 5924.
A. M. DiLauro, A. Abbaspourrad, D. A. Weitz and S. T. Phillips, Macromolecules, 2013, 46, 3309.
A. W. Knoll, D. Pires, O. Coulembier, P. Dubois and J. L. Hedrick, Adv. Mater., 2010, 22, 3361.
B. Fan and E. R. Gillies, Mol. Pharmaceutics, 2017, 14, 2548.
A. Gandini, Prog. Polym. Sci., 2013, 38, 1.
T. T. N'Guyen, H. T. Duong, J. Basuki, V. Montembault, S. Pascual, C. Guibert, J. Fresnais, C. Boyer, M. R. Whittaker and T. P. Davis, Angew. Chem., Int. Ed., 2013, 52, 14152.
W. Agut, A. Brulet, D. Taton, O. Sandre and S. Lecommandoux, Soft Matter, 2011, 7, 9744.

THERMALLY SENSITIVE PROTECTING GROUPS FOR CYSTEINE, AND MANUFACTURE AND USE THEREOF

RELATED APPLICATIONS

This application is a continuation of prior U.S. application Ser. No. 16/985,815 filed 5 Aug. 2020, which claims the benefit of 35 USC § 119(e) to U.S. Provisional Application Ser. No. 62/883,332 filed 6 Aug. 2019.

SCOPE OF THE INVENTION

The present invention relates to a protected cysteine residue having a protecting group bonded to a thiol side chain thereof, and which is configured to permit deprotection at a preselected temperature. The present invention also relates to a method for producing the protected cysteine residue, and a method for synthesizing a peptide containing a plurality of cysteines and using the protected cysteine residues to sequentially generate a plurality of specific disulfide bonds.

BACKGROUND OF THE INVENTION

Peptide synthesis involves formation of amide bonds between multiple amino acids by the condensation reaction of the carboxyl group of one amino acid with the amino group of another amino acid. To synthesize a peptide of specific amino acid sequence, solid phase peptide synthesis may be used to form a peptide chain using successive reaction and introduction of preselected amino acids to a solid insoluble and porous support, which includes a polymeric resin bead having a reactive linker group for attaching a growing peptide chain. The reactive linker group may include an amino group, and the amino acids to be introduced to the solid support may be protected on the N-terminus (and possibly the side chain as needed), using known protecting groups, such as tert-Butyloxycarbonyl (Boc) or fluorenylmethyloxycarbonyl (Fmoc) protecting group.

Solid phase peptide synthesis may involve repeated cycles of coupling and N-terminal deprotection reactions, with washing of the resin bead between each cycle. Specifically, a first N-terminus protected amino acid is coupled to the amino group of the reactive linker group in the solid support, and the amino acid is deprotected to leave the amino functional group of the amino acid available to form an amide bond with a second N-terminus protected amino acid. The cycles are repeated with a preselected sequence of amino acids, and until the peptide of the desired length and sequence is formed. The peptide as formed is then cleaved from the solid support, isolated and purified, and may be subject to further treatment.

Aside from the primary peptide sequence which may be obtained with solid phase peptide synthesis and which will fold into defined secondary structures, disulfide bonds play an important role in the organization of proteins and peptides, such as determining the ternary structure. Formation of correct disulfide bonds between correct cysteine residues may thus facilitate formation of correct three-dimensional structure, especially in short peptides. Disulfide bonds may however present challenges in synthesizing peptides and proteins by way of biotransformations; while the linear sequence may be readily programmed into DNA, the information regarding which disulfide bonds should be formed is often regulated by additional factors and is part of the post-translational modifications.

It has been recognized that a synthesized peptide intended to function as a natural peptide of the same amino acid sequence and with specific disulfide bonds may require further treatment during and after peptide synthesis to ensure that the synthesized peptide possesses the same natural disulfide bonds. Previously, orthogonal protection of the thiol side chains (involved in forming disulfide bonds) of cysteine residues have been used to effect selective deprotection and disulfide bond formation after peptide synthesis. Specifically, a crude peptide is formed with cysteine residues having their respective thiol side chains protected with a protecting group, such as acetamidomethyl, tert-butyl, 3-nitro-2-pyridine sulfenyl, 2-pyridine-sulfenyl or trityl, and which remains on the thiol side chains after peptide synthesis. By having each pair of specific cysteine residues intended to form a disulfide bond having orthogonal protection independent from other pairs of cysteine residues, it has been possible to successively deprotect different pairs of cysteine residues and introduce regioselectivity to disulfide bond formation.

Peptide synthesis may thus employ multiple pairs of cysteine protecting groups, in cases where multiple cysteine bonds are desired. A bioactive peptide ordinarily possesses both the linear amino acid sequence and the specific disulfide bonds made in the naturally-occurring material, which if present contribute to the three dimensional structure. For example, if there are 8 cysteines in a short peptide, these would make 4 disulfide bonds, and there would be 70 (8!4) possible structures containing 4 disulfide bonds that can be generated, where only 1 is the desirable compound. Such need for increasing degrees of orthogonality between protecting groups increases the complexity of the peptide, and requires specialist and fine-tuning of peptide synthesis conditions, as well as iterative cycles of reaction and purification to isolate the desired compound and remove the unwanted reagents. This is a slow, costly and inefficient process, which may lead to low yields and complex purification problems, and which may effectively prohibit scalability to produce larger amounts of the desired peptide.

An improvement may reside with use of a common class of protecting groups that are removed under the same trigger and differ from one another only by the threshold level of that trigger. This may preferably involve only a single reagent introduced to the reaction mixture, with slow increase of its concentration. An existing example involves use of acid-sensitive end-caps, although such approach has two complications: the acidic conditions used for deprotection are not compatible with the conditions required to dimerize the cysteine residues, and the dynamic range between the acid-sensitivity of the protecting groups is insufficient to provide the required levels of selectivity, with chemistry relegated between a pH of 0 and 5, sufficient for no more than three different acid-sensitive protecting groups (e.g. triggered at pH=0, 2.5 and 5). However, 2.5 pH units may not provide sufficient discrimination in reaction rates to ensure complete selectivity, and being triggered at pH 5 may result in background cleavage at neutral pH and may also limit synthetic operations available to the chemist making the peptide.

It has thus been appreciated that known regioselective formation of disulfide bonds may be associated with greater costs, time and complexity and reduced yield and selectivity, often stemming from the need to develop customized residues and protecting groups, and in the absence of any general approach to providing orthogonal protection.

SUMMARY OF THE INVENTION

It is a non-limiting object of the present invention to provide a protecting group for protecting a cysteine residue and permitting more regioselective formation of multiple disulfide bonds during peptide synthesis, and which includes a Diels-Alder cycloadduct of an optionally substituted furan and an optionally substituted maleimide, and optionally a cyclization spacer for placement between the thiol side chain and the Diels-Alder cycloadduct.

It is another non-limiting object of the present invention to provide a protecting group for protecting a cysteine residue for use in peptide synthesis, and which may permit deprotection in response to a single physical change, such as the temperature, without necessary requiring use of multiple reagents.

It is another non-limiting object of the present invention to provide a protecting group for protecting a cysteine residue for use in peptide synthesis, and which may permit configuration to obtain a family of different protecting groups selected for deprotection at different temperatures, so as to allow the peptide synthesis in a single pot without necessary requiring isolation and purification steps between formation of multiple disulfide bonds.

It is another non-limiting object of the present invention to provide a protected cysteine residue for preparing a synthetic peptide or protein having a three dimensional structure, and which may permit ready incorporation into synthetic peptide synthesis to form two or more preselected disulfide bonds to facilitate achieving the three dimensional structure.

It is another non-limiting object of the present invention to provide a process for synthesizing a peptide or protein having two of more preselected disulfide bonds, and which includes increasing a reaction temperature to effect sequential deprotection of protected cysteine residue pairs to form the preselected disulfide bonds, without necessarily requiring use deprotection reagents or separation or purification steps.

It is another non-limiting object of the present invention to provide a process for synthesizing a peptide having two of more preselected disulfide bonds, and which may permit formation of functioning peptides with reduced production of by-products having disulfide bonds other than the preselected disulfide bonds, and which may be adopted for a larger scale production of a peptide of commercial value, such as insulin or the conotoxins, or a library of disulfide-containing research peptides.

In one simplified aspect, the present invention provides a protecting group for protecting the thiol side chain of a cysteine residue, the protecting group comprising a Diels-Alder cycloadduct, either the endo or exo diastereomer, or a mixture of the two, of a furan and a maleimide, and optionally, a linker interposed between the thiol side chain and the Diels-Alder cycloadduct. It is to be appreciated that the furan, the maleimide and the linker are optionally substituted.

In one aspect, the present invention provides a compound having structural formula 1 or 2:

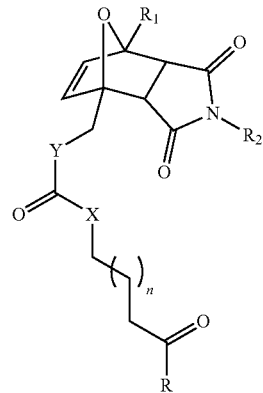

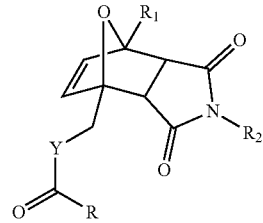

wherein R is an electron withdrawing group or a leaving group; X and Y are independently of each other oxygen, sulfur, nitrogen or phosphorus; $R_1$ and $R_2$ are independently of each other hydrogen, hydroxyl, halo, alkyl, alkenyl, alkynyl, cycloalkyl, heterocycloalkyl, aryl, aralkyl, heteroaryl, heteroaralkyl, formyl, haloformyl, carbonyl, carboxyl, alkoxy, alkoxycarbonyl, (alkoxycarbonyl)oxy, carbamoyl, amino, amido, imino, imido, azo, cyanato, isocyanato, cyano, nitro, sulfanyl, thiocyanato or phosphono, each of which is optionally substituted; and n is an integer between 1 and 12, inclusive.

In another aspect, the present invention provides a protecting group for protecting a cysteine residue, the protecting group having structural formula 1 or 2:

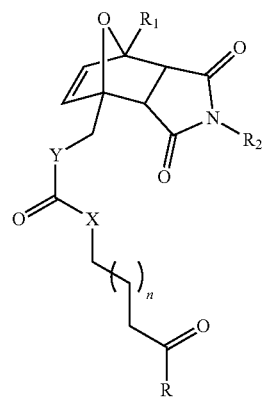

-continued

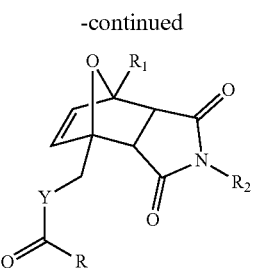

wherein R is an electron withdrawing group or a leaving group; X and Y are independently of each other oxygen, sulfur, selenium, nitrogen or phosphorus; $R_1$ and $R_2$ are independently of each other hydrogen, hydroxyl, halo, alkyl, alkenyl, alkynyl, cycloalkyl, heterocycloalkyl, aryl, aralkyl, heteroaryl, heteroaralkyl, formyl, haloformyl, carbonyl, carboxyl, alkoxy, dialkoxy, trialkoxy, alkoxycarbonyl, (alkoxycarbonyl)oxy, carbamoyl, amino, amido, ammonio, imino, imido, azido, azo, cyanato, isocyanato, nitroxy, cyano, isocyano, nitrosooxy, nitro, nitrosyl, (carbamoyl)oxy, sulfanyl, disulfanyl, alkylsulfanyl, sulfinyl, sulfonyl, sulfoamido, sulfino, thiocyanate, isothiocyanato, thioyl, methanethioyl, mercaptocarbonyl, hydroxyl(thiocarbonyl), dithiocarboxy, phosphanyl or phosphono; and n is an integer between 1 and 12, inclusive. It is to be appreciated that R, $R_1$ and $R_2$ are optionally substituted.

In yet another aspect, the present invention provides a protecting group for protecting a cysteine residue, the protecting group having structural formula 1 or 2:

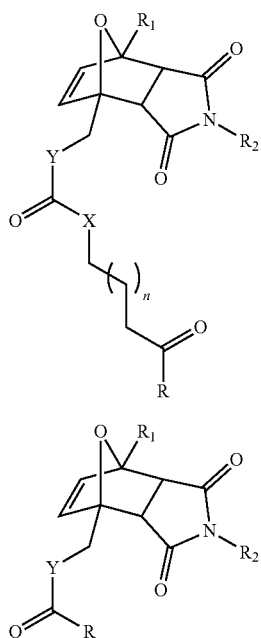

wherein R is an electron withdrawing group or a leaving group; X and Y are independently of each other oxygen, sulfur, nitrogen or phosphorus; $R_1$ and $R_2$ are independently of each other hydrogen, hydroxyl, halo, alkyl, alkenyl, alkynyl, cycloalkyl, heterocycloalkyl, aryl, aralkyl, heteroaryl, heteroaralkyl, formyl, haloformyl, carbonyl, carboxyl, alkoxy, alkoxycarbonyl, (alkoxycarbonyl)oxy, carbamoyl, amino, amido, imino, imido, azo, cyanato, isocyanato, cyano, nitro, sulfanyl, thiocyanato or phosphono, each of which is optionally substituted; and n is an integer between 1 and 12, inclusive.

In one embodiment, R is an activated ester or acid; X is sulfur, oxygen or nitrogen; Y is oxygen or sulfur; $R_1$ and $R_2$ are independently of each other alkyl, aryl, a halogen, an ether, a thioether, a dialkylamine or trialkylammonium, an ester or an acid derivative thereof, or a ketone; and n is an integer between 1 and 9, inclusive.

In one embodiment, $R_1$ and $R_2$ are independently of each other hydrogen, hydroxyl, halo, alkyl, alkenyl, alkynyl, cycloalkyl, heterocycloalkyl, aryl, aralkyl, heteroaryl, heteroaralkyl, formyl, haloformyl, carbonyl, carboxyl, alkoxy, alkoxycarbonyl, (alkoxycarbonyl)oxy, carbamoyl, amino, imino, imido, azo, cyanato, isocyanato, nitroxy, cyano, isocyano, nitro, sulfanyl, alkylsulfanyl, sulfinyl, sulfino, thiocyanate or isothiocyanato. In one embodiment, $R_1$ and $R_2$ are independently of each other hydrogen, hydroxyl, halo, alkyl, cycloalkyl, heterocycloalkyl, aryl, heteroaryl, formyl, carbonyl, carboxyl, alkoxy, alkoxycarbonyl, carbamoyl, amino, nitro or alkylsulfanyl.

In one embodiment, $R_1$ is hydrogen, hydroxyl, halo, alkyl, formyl, carbonyl, carboxyl, alkoxy, alkoxycarbonyl, amino or nitro. In one embodiment, $R_1$ is hydrogen, nitro, halo or alkoxy, preferably, hydrogen, nitro, bromo, chloro, fluoro, nitro, methoxy or ethoxy, or more preferably, hydrogen, nitro, bromo or methoxy. In one embodiment, $R_2$ is alkyl or aryl. In one embodiment. $R_2$ is methyl, ethyl, propyl, butyl or phenyl. In one embodiment, $R_2$ is p-methoxyphenyl, p-nitrophenyl or benzyl.

In one embodiment, $R_1$ and $R_2$ are independently of each other hydrogen, hydroxyl, halo, alkyl, cycloalkyl, heterocycloalkyl, aryl, heteroaryl, formyl, carbonyl, carboxyl, alkoxy, amino or nitro, each of which is optionally substituted. In one embodiment, $R_1$ is hydrogen, hydroxyl, halo, alkyl, formyl, carbonyl, carboxyl, alkoxy, alkoxycarbonyl, amino or nitro, each of which is optionally substituted, and $R_2$ is hydrogen, alkyl, cycloalkyl, heterocycloalkyl, aryl or heteroaryl, each of which is optionally substituted. In one embodiment, $R_1$ is hydrogen, nitro, halo or alkoxy, and $R_2$ is alkyl, aryl or heteroaryl, each of which is optionally substituted. In one embodiment, $R_1$ is hydrogen, nitro, bromo, chloro, fluoro, methoxy or ethoxy, and $R_2$ is methyl, ethyl, propyl, butyl, phenyl, p-methoxyphenyl, p-nitrophenyl or benzyl.

In one embodiment, X and Y are independently of each other oxygen or nitrogen. In one embodiment, X is nitrogen and Y is oxygen.

In one embodiment, n is an integer between 1 and 4, inclusive.

In one embodiment, R being the electron withdrawing group or the leaving group is as defined below. In one embodiment, R is hydroxyl, alkyl, alkenyl or halo. In one embodiment, R is hydroxyl, chloro, methyl or allyl.

In one embodiment, $R_1$ is substituted aryl, preferably 4-methoxyphenyl, 4-nitrophenyl, 4-fluorophenyl, 4-trifluoromethylphenyl, 4-cyanophenyl, 4-chlorophenyl, 4-bromophenyl, 4-iodophenyl, 4-di-N,N-methylaminophenyl, 4-(methoxycarbonyl)phenyl, 3-methoxyphenyl, 3-nitrophenyl, 3-fluorophenyl, 3-trifluoromethylphenyl, 3-cyanophenyl, 3-chlorophenyl, 3-bromophenyl, 3-iodophenyl, 3-di-N,N-methylaminophenyl or 3-(methoxycarbonyl)phenyl. In one embodiment, $R_2$ is propargyl, alkylazido, 4-azidophenyl, 4-alkynylphenyl or 4-propargyphenyl. In one embodiment, R is OH, Cl, 4-nitrophenoxyl, Br, succinyl or other leaving group.

It is to be appreciated that compound 1 or 2 preferably comprises a Diels-Alder cycloadduct portion which may exist in an endo or exo stereoisomeric form. It is to be also appreciated that compound 1 or 2 may include a mixture of the endo and exo stereoisomers in different proportions. In one embodiment, compound 1 or 2 contains, or is purified to contain, a greater portion of the endo or exo stereoisomer, preferably the endo stereoisomer. In one embodiment, compound 1 or 2 contains 90 weight % or more, preferably 95 weight % or more, more preferably 97% or more, or most preferably 99% or more of the endo or exo stereoisomer, or preferably the endo stereoisomer, based on the total weight of compound 1 or 2.

In another aspect, the present invention provides a method for preparing a protecting group, preferably compound 1 or compound 2, the method including conducting a Diels-Alder reaction between a furan of structural formula 5 and a maleimide of structural formula 6 to produce a cycloadduct of structural formula 7:

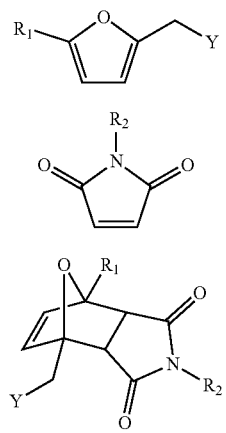

wherein $R_1$, $R_2$ and Y are as defined herein in respect of compound 1 or 2. It is to be appreciated that Y included in the furan of formula 5 or the cycloadduct of formula 7 may additionally include one or more hydrogens or other substituents to satisfy the octet rule. Preferably, the furan of formula 5 is a hydroxymethyl furan, i.e., Y is oxygen bonded to a hydrogen (hydroxyl).

In one embodiment, the Diels-Alder reaction is conducted at a reaction temperature between about 0° C. and about 160° C., preferably between about 0° C. and about 120° C. or more preferably between about 0° C. and about 90° C. in a solvent for a reaction time of between about 10 seconds and about 96 hours, preferably between about 5 minutes and about 72 hours or more preferably between about 15 minutes and about 48 hours. In one embodiment, the solvent is one or more of benzene, acetonitrile, chloroform, dichloromethane, tetrahydrofuran, DMSO, DMF, toluene, xylene, hydrocarbon solvents, dichloroethane, tetrachloroethane, dioxane, methanol and isopropanol.

It is to be appreciated that the cycloadduct of formula 7 may include endo and exo cycloadducts. In one embodiment, the method further comprises separating the endo and exo cycloadducts, preferably using thin layer chromatography, column chromatography, high performance liquid chromatography (HPLC), cyclotron or crystallization from a crystallization solvent. In one embodiment, said separating the endo and exo cycloadducts comprises separating the endo and exo cycloadducts to obtain the endo cycloadduct.

In one embodiment, the method further comprises activating Y with an activating reagent, preferably to obtain an activated compound or compound 2. In one embodiment, the activated compound comprises an activated ester or acid coupled to Y, or preferably, an acyl halide, carboxyl, succinamyl (2,5-dioxo-1-pyrrolidinyl) carbonic ester or alkoxycarbonyl coupled to Y, wherein said acyl halide comprises —F, —Cl, —Br or —I, or preferably, the acyl halide is chloroformyl or bromoformyl. In one embodiment, the activating reagent comprises phosgene, diphosgene, triphosgene, 4-nitrophenylchloroformate or carbonyl diimidazole.

In one embodiment, the method further comprises coupling a linker to the activated compound or compound 2 to obtain compound 1, wherein the linker is preferably a compound of structural formula 8:

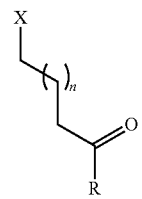

wherein X, R and n are as defined above in respect of compound 1. In one embodiment, one or both of X and R are alkylamino.

In an alternative embodiment, the linker comprises optionally substituted straight chain or branched alkyl having a pair of functionalized ends, wherein one said end is functionalized with a nucleophilic heteroatom and the other said end is functionalized with carboxyl or protected or masked carboxyl, and wherein the alkyl of the linker comprises 3 to 10 methylene groups between the functionalized ends. In one embodiment, the nucleophilic heteroatom is amino, hydroxyl or thiol. In one embodiment, the linker is a cyclization spacer.

In yet another aspect, the present invention provides a cysteine residue for use in peptide synthesis, preferably solid phase peptide synthesis or more preferably Fmoc or Boc solid phase peptide synthesis, the cysteine residue having structural formula 3:

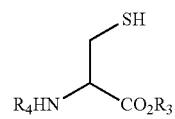

wherein $R_4$ is Fmoc or Boc, and $R_3$ is a protecting group compatible with coupling of the protecting group on the thiol side chain.

In one embodiment, $R_3$ is allyl, tert-butyldimethylsilyl or TBS, methoxymethyl or MOM, ethoxymethyl or EOM, methyl, p-methoxybenzyl or p-nitrobenzyl. In one embodiment, $R_3$ is not a thermally labile or hydrogenolysis-labile protecting group. In one embodiment, the cysteine residue is selected for use with compound 1 or 2.

In one preferred embodiment, compound 3 having as $R_4$ Fmoc and as $R_3$ allyl is prepared from a commercially available compound 4 through sequential allyl protection and trityl deprotection;

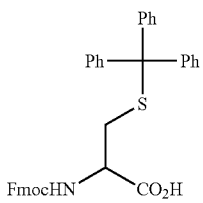

It is to be appreciated that the cysteine residue may include an L-cysteine, a D-cysteine or a combination thereof.

In yet another aspect, the present invention provides a protected cysteine residue for peptide synthesis, the protected cysteine residue having structural formula 9 or 10:

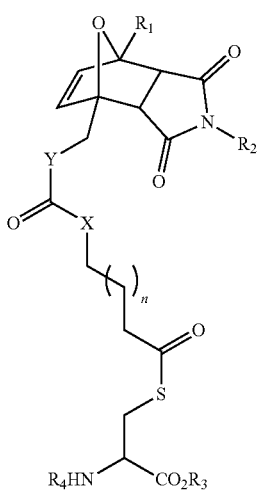

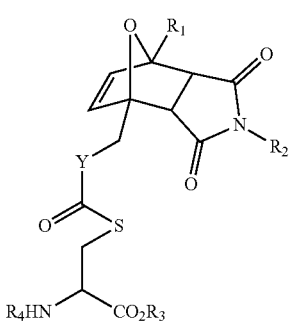

wherein $R_1$ to $R_4$, X, Y and n are as defined herein.

In yet another aspect, the present invention provides a protected cysteine having structural formula 9 or 10:

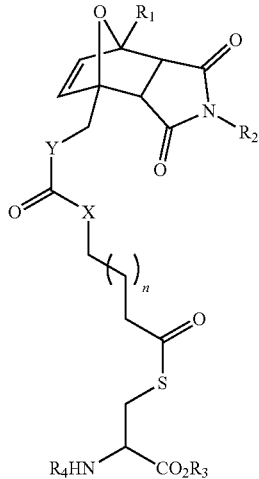

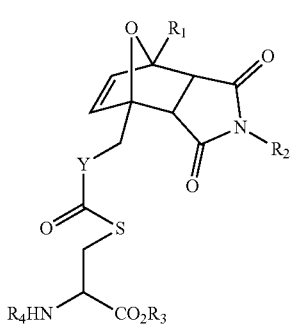

wherein X and Y are independently of each other oxygen, sulfur, nitrogen or phosphorus; $R_1$ and $R_2$ are independently of each other hydrogen, hydroxyl, halo, alkyl, alkenyl, alkynyl, cycloalkyl, heterocycloalkyl, aryl, aralkyl, heteroaryl, heteroaralkyl, formyl, haloformyl, carbonyl, carboxyl, alkoxy, alkoxycarbonyl, (alkoxycarbonyl)oxy, carbamoyl, amino, amido, imino, imido, azo, cyanato, isocyanato, cyano, nitro, sulfanyl, thiocyanato or phosphono, each of which is optionally substituted; $R_3$ and $R_4$ are independently each other hydrogen or a protecting group; and n is an integer between 1 and 12, inclusive.

In one embodiment, $R_3$ and $R_4$ are independently each other hydrogen, alkyl, allyl, tert-Butyloxycarbonyl (Boc), fluorenylmethyloxycarbonyl (Fmoc), tert-butyldimethylsilyl (TBS), methoxymethyl (MOM), ethoxymethyl (EOM), p-methoxybenzyl or p-nitrobenzyl. In one embodiment, $R_3$ is hydrogen or allyl and $R_4$ is Fmoc.

In one embodiment, R is an electron withdrawing group selected to facilitate coupling of the protecting group to the thiol side chain of the cysteine residue. In one embodiment, the electron withdrawing group is selected to draw electrons from the adjacent carbonyl or the carbon atom thereof. In one embodiment, the electron withdrawing group is selected to draw electrons from the adjacent carbonyl to facilitate a substitution reaction with the thiol side chain, wherein in the substitution reaction, the electron withdrawing group is replaced by the thiol side chain. In one embodiment, the electron withdrawing group is a group selected to reduce electron density of the moiety to which it is attached (relative to the density of the moiety without the substituent). In one embodiment, the electron withdrawing group is nitro, haloalkyl, halo, formyl, haloformyl, alkanoyl, alkylsulfonyl, cyano, alkylsulfinyl, carboxyl, alkoxycarbonyl, sulfonamido, amido, CONR$^{10}$R$^{20}$, wherein R$^{10}$ and R$^{20}$ are independently of each other hydrogen, alkyl, aryl, arylalkyl, heterocycloalkyl or cycloalkyl.

In one embodiment, R is a leaving group selected to facilitate coupling of the protecting group to the thiol side chain of the cysteine residue. In one embodiment, the leaving group is a species or moiety selected to detach from the protecting group during a reaction, such as a substitution reaction. In one embodiment, the leaving group is dinitrogen, triflate, halogen, hydroxyl, amino, alkoxy, acyloxy (preferably —OAc, —OC(O)CF$_3$), sulfonate (preferably mesyl or tosyl), acetamide (preferably —NHC(O)Me), carbamate (preferably N(Me)C(O)Ot-Bu), phosphonate (preferably —OP(O)(OEt)$_2$) or alcohol.

In one embodiment, X is sulfur, oxygen or nitrogen, and Y is oxygen or sulfur, preferably, X is nitrogen and Y is oxygen.

In one embodiment, the term "alkyl" refers to a straight-chained or branched hydrocarbon group containing 1 to 12 carbon atoms. The alkyl may include lower alkyl, referring to a C1-C6 alkyl chain. Examples of the alkyl group include methyl, ethyl, n-propyl, isopropyl, tert-butyl, and n-pentyl. The Alkyl group may be optionally substituted with one or more substituents.

In one embodiment, the term "alkenyl" refers to an unsaturated hydrocarbon chain that may be a straight chain or branched chain, containing 2 to 12 carbon atoms and at least one carbon-carbon double bond. The Alkenyl group may be optionally substituted with one or more substituents. In one embodiment, the term "alkynyl" refers to an unsaturated hydrocarbon chain that may be a straight chain or branched chain, containing 2 to 12 carbon atoms and at least one carbon-carbon triple bond. The alkynyl groups may be optionally substituted with one or more substituents. The sp$^2$ or sp carbons of the alkenyl or alkynyl group may optionally be the point of attachment of the group.

In one embodiment, the term "alkylene" refers to an alkyl group that has two points of attachment, and may preferably include (C1-C6) alkylene. In one embodiment, the alkylene is methylene, ethylene, n-propylene or isopropylene.

In one embodiment, the term "amino" refers to a functional group having a nitrogen atom bonded to two hydrogen atoms, where one or both of the hydrogen atoms may optionally be substituted, preferably but not limited to, alkyl or aryl, i.e., the amino includes primary, secondary, tertiary or quaternary amino. For instance, the amino includes alkylamino, dialkylamino or trialkylamino.

In one embodiment, the term "cycloalkyl" refers to a hydrocarbon 3-8 membered monocyclic or 7-14 membered bicyclic ring system having at least one non-aromatic ring. The Cycloalkyl group is optionally substituted with one or more substituents, and may be cyclopropyl, cyclopentyl, cyclohexyl, cyclobutyl, cycloheptyl, cyclooctyl, cyclononyl or cyclodecyl.

In one embodiment, the term "heterocycloalkyl" refers to a nonaromatic 5-8 membered monocyclic, 8-12 membered bicyclic or 11-14 membered tricyclic ring system comprising 1-3 heteroatoms if monocyclic, 1-6 heteroatoms if bicyclic or 1-9 heteroatoms if tricyclic, said heteroatoms being O, N, S, B, P or Si. The heterocycloalkyl is optionally substituted with one or more substituents. In one embodiment, the heterocycloalkyl is piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl or thiirene.

In one embodiment, the term "aryl" refers to a hydrocarbon monocyclic, bicyclic or tricyclic aromatic ring system, and which is optionally substituted with one or more substituents. In one embodiment, the aryl is phenyl, naphthyl, anthracenyl, fluorenyl, indenyl or azulenyl.

In one embodiment, the term "aralkyl" refers to aryl attached to another group by a (C1-C6)alkylene group. The aralkyl is optionally substituted, either on the aryl portion or the alkylene portion of the aralkyl, with one or more substituent. In one embodiment, the aralkyl is benzyl, 2-phenyl-ethyl or naphth-3-yl-methyl.

In one embodiment, the term "heteroaryl" refers to an aromatic 5-8 membered monocyclic, 8-12 membered bicyclic or 11-14 membered tricyclic ring system having 1-4 ring heteroatoms if monocyclic, 1-6 heteroatoms if bicyclic or 1-9 heteroatoms if tricyclic, where the heteroatoms are independently O, N or S, and the remainder ring atoms are carbon. The heteroaryl is optionally substituted with one or more substituents.

In one embodiment, the heteroaryl is pyridyl, 1-oxo-pyridyl, furanyl, benzo[1,3]dioxolyl, benzo[1,4]clioxinyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo[b]thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl or pyrrolo[2,1b]oxazolyl.

In one embodiment, the term "heteroaralkyl" or "heteroarylalkyl" means a heteroaryl group attached to another group by a (C1-C6)alkylene. The heteroaralkyl may be optionally substituted, either on the heteroaryl portion or the alkylene portion of the heteroaralkyl, with one or more substituent. In one embodiment, the heteroaralkyl is 2-(pyridin-4-yl)-propyl, 2-(thien-3-yl)-ethyl or imidazol-4-yl-methyl.

In one embodiment, the term "alkoxy" refers to an —O-alkyl radical.

In one embodiment, the term "ester" refers to a —C(O)OR$^{30}$, wherein R$^{30}$ is preferably alkyl or aryl.

In one embodiment, the term "halogen" or "halo" is —F, —Cl, —Br or —I. In one embodiment, the term "haloalkyl" is an alkyl group in which one or more hydrogen radicals are replaced by halogen, and may include perhaloalkyl. In one embodiment, the haloalkyl is trifluoromethyl, difluoromethyl, bromomethyl, 1,2-dichloroethyl, 4-iodobutyl or 2-fluoropentyl.

In one embodiment, the term "substituent" or "substituted" means that a hydrogen radical is replaced with a group that does not substantially adversely affect the stability or activity of the compound. The term "substituted" refers to one or more substituents, which may be the same or different, each replacing a hydrogen atom. In one embodiment, the substituent is halogen, hydroxyl, amino, alkylamino, arylamino, dialkylamino, diarylamino, cyano, nitro, mercapto, oxo, carbonyl, thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, aryl, heteroaryl, cyclyl and heterocyclyl are optionally substituted with alkyl, aryl, heteroaryl, halogen, hydroxyl, amino, mercapto, cyano, nitro, oxo, thioxo or imino.

It is to be appreciated that specific moieties recited in the definitions of the above variable groups, including, but not limited to, R and $R_1$ to $R_4$, may be optionally substituted.

BRIEF DESCRIPTION OF THE DRAWINGS

Reference may now be had to the following detailed description taken together with the accompanying drawings in which.

DETAILED DESCRIPTION OF THE PREFERRED EMBODIMENTS

Figure 1:
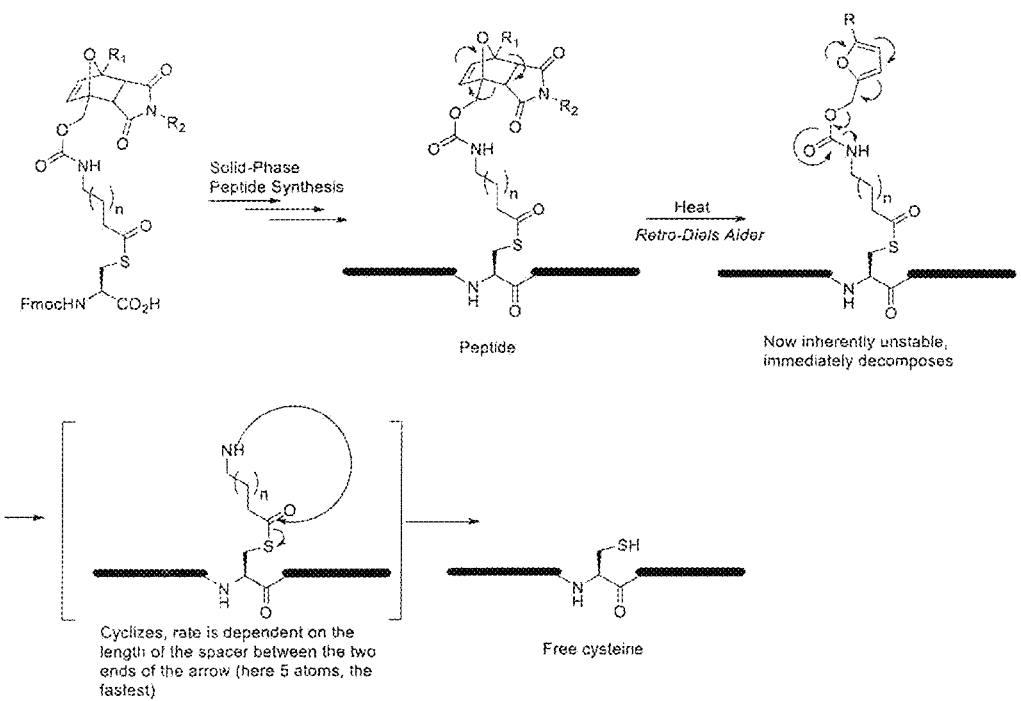
FIG. 1 is a reaction mechanism illustrating a process for synthesizing a peptide in accordance with a preferred embodiment of the present invention, and which involves solid-phase synthesis of the peptide with a protected cysteine residue and subsequent deprotection of the protected cysteine residue to produce a free cysteine available to form a disulfide bond.

In one aspect, the invention provides a set of cysteine building blocks for solid-phase peptide synthesis designed for the selective formation of disulfide bonds after synthesis. They can be incorporated into normal peptide synthesis using either Fmoc or Boc strategies (accounting for >99% of all syntheses) without necessarily requiring any need for modification or customization.

It has been recognized disulfide bonds may be essential for biological activity of peptides and proteins, and may assist organizing the three-dimensional shape. The peptide synthesis gives us the linear order of amino acids but does not in and of itself help us make the three-dimensional shapes. To make the three-dimensional shapes, you need to make the disulfide bonds after the peptide synthesis. This may require selectively deprotecting each pair of cysteines in turn, and thus requiring many different pairs of protecting group strategies if you have multiple disulfide bonds, as well as special reagents and very expensive, customized residues that need to be developed, tested, and evaluated for each specific case, as there are no general solutions currently.

This means everything must be redesigned every time, although it has been proposed that escalating conditions can be used to control selective deprotection. Acid-sensitive protecting groups are potentially the best candidates, with the idea being that a protecting group that cleaves at pH 5 will cleave 100-times faster than one that cleaves at 3, which in turn will cleave 100-times faster than one that cleaves at 1. It has been recognized however that the problem with this approach is that 100-times is often insufficient, and in this case you are limited to three pairs of protecting groups; this means that this approach has not worked very well. Finally, there may be a lot of unintentional deprotection during synthesis because neutral conditions will still result in cleavage. The publication "Direct palladium-mediated on-resin disulfide formation from Allocam protected peptides", *Organic & Biomolecular Chemistry*, 15.14 (2017): 2914-2918 to Stockdill reports using allylation chemistry to selectively deprotect cysteines, but the required levels of discrimination were not possible to achieve, and the reaction requires a lot of some very expensive reagents (metallic palladium) that need to be removed from the reaction mixture prior to biological use.

Therefore, it has been appreciated that a preferred approach may allow for a one-pot sequential and selective formation of the required disulfide bonds with no or less reagents needed, and no or less purifications or changes in the reaction mixture composition over the course of the reaction. It has been recognized that one possibility for a reagent-free approach may use heat. Most stable chemical bonds may not be highly heat-sensitive, however, retro-cycloadditions can be highly temperature sensitive, including Diels-Alder cycloadducts formed between dienes and dienophiles.

The applicant has recognized that reactions between furans and maleimides may be promising due to near-physiological temperatures which may be involved in the retro-Diels-Alder reaction. It has been envisioned that this may be due to a combination of a highly favored forward reaction with a very low lying lowest unoccupied molecular orbital or LUMO for the maleimide, and a favorable reverse reaction as furan is aromatic. It has also been envisioned that the precise thermodynamics and the temperature required to overcome the reversible energy barrier may be modulated through adjusting the electronics of the transition states of the reaction, and by changing the substituents on the furan and maleimide.

It has been envisioned that a process for synthesizing a peptide using the protected cysteine residue of the invention may be practiced "reagent-free" or with a reduced number of required reagents, and with use of heat as the stimulus for deprotection and formation of disulfide bonds. To get around the background cleavage issue, it may be possible to raise the initial temperature to 60° C., which may provide background cleavage at ambient temperature (23° C.) at about 2000 times slower than at 60° C. The following preferred non-limiting protected cysteine residue may decompose at different temperatures to allow for disassembly, while being reasonably stable at room temperature or at least sufficiently stable to handle and use for peptide synthesis:

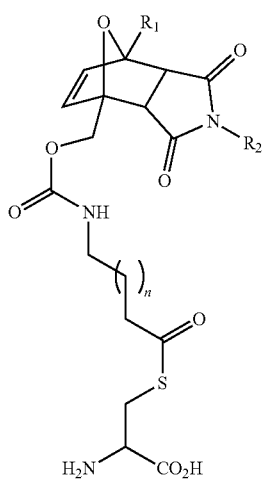

wherein $R_1$ is hydrogen, nitro, bromine or methoxy, and $R_2$ is p-methoxyphenyl, p-nitrophenyl or benzyl. The above preferred non-limiting cysteine residue is protected with a protecting group having two components, or namely a Diels-Alder cycloadduct of furan and maleimide and a linker or cyclization spacer interposed between the thiol side chain and the Diels-Alder adduct.

It has been recognized that some background cleavage may remain if one set of protecting groups cleave at 60° C., and the second at 80° C. So, the protecting group of the current invention most preferably incorporates the Diels-Alder cycloadduct coupled with a second gating mechanism, or namely a cyclization spacer. It has been recognized that smaller rings (for instance, down to 5 atoms) form faster than larger rings. So, a low temperature trigger coupled with a 5-membered spacer may liberate a cysteine much faster than a mid-temperature trigger with a 6-membered spacer (the 5-membered ring closes about 100-times faster than a 6-membered ring, which in turn is 100 times faster than a 7, which is about 100-times faster than an 8, which is 1000 times faster than a 9; differentiation between ring sizes may cease to significantly matter much beyond this point). Consequently, even if the higher temperature thermally-active protecting group falls off at a lower temperature than expected, the liberated cyclization spacer is less likely to cyclize, and the cysteine will not be easily liberated. This dual gating may permit each pair of cysteines to be liberated or deprotected in turn, and will then dimerize to provide the disulfide bond before the next pair of cysteines is liberated.

The applicant has appreciated that consequently, the deprotection reaction may proceed without the need for any change in conditions, except for a gradual increase in temperature. The products of the reactions may be innocuous, and may include for example a maleimide, a furan and a cyclic lactam, which may be readily separated from the peptide by precipitation of the resulting peptide or an aqueous-organic extraction to remove the organic-soluble byproducts from the reaction mixture. A sacrificial amount of hindered thiol may be required to scavenge the maleimide if maleimide-thiol reactions are a possible complication in specific cases, although the high dilution of these reaction mixtures renders this an uncommon prospect as the two cysteines in the molecule are held in close proximity.

It has been envisioned that while slow reaction rates of the different cyclization spacers may potentially lead to problems, this may be counteracted by slowly increasing temperature, i.e., as the temperature rises, the rates of reactions increase, and a spacer that is slow to cyclize at 60° C. will cyclize far faster at 80 or 100° C. With different combinations of the Diels-Alder cycloadduct with varying substituents and the cyclization spacer with varying lengths, it may be possible to devise a series of protecting groups that will be thermally triggerable at 15 to 20° C. increments starting at 45° C., and allow for the formation of 5 different systems, preferably triggerable at 45° C., 60° C., 75° C., 90° C. and 105° C., within reasonable temperature ranges. It is expected the higher temperatures may denature large proteins, and the current invention may preferably encompass processes for synthesizing peptides, such as insulin and the non-addictive conotoxin pain-killers, where the higher temperatures are not expected to be significantly problematic. The applicant has recognized that the higher temperature ranges are often used during peptide synthesis in the microwave reactors attached to many modern peptide synthesis machines. Finally, the cyclization could occur before cleavage from the solid-support, further simplifying purification and improving yields.

Reference is made to FIG. 1 which illustrates a reaction pathway for deprotection of the protected cysteine residue after peptide synthesis. First, a crude peptide was synthesized with Fmoc-protected amino acids, including an Fmoc-protected cysteine shown in FIG. 1 with a protecting group having a 7-oxanorbornene construct with $R_1$ and $R_2$, coupled with a cyclization spacer having the variable length n. While not wishing to be bound by a theory, it has been appreciated that the 2-methylsubstituted furan ring forming part of the protecting group may possess natural instability which may be masked when incorporated as part of the 7-oxanorbornene construct with maleimide, and with thermal decomposition of that construct, the unstable 2-methylsubstituted furan ring is removed from the cyclization spacer.

Figure 2:
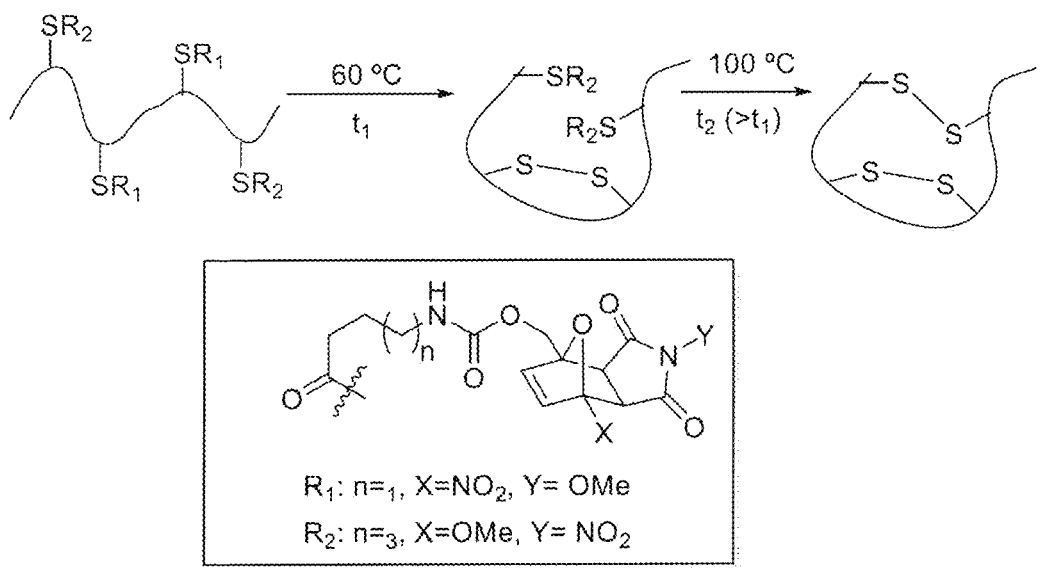
FIG. 2 is a scheme illustrating a process for synthesizing a peptide in accordance with a preferred embodiment of the present invention, and which involves formation of two disulfide bonds at 60° C. and 100° C.

Reference is made to FIG. 2 which illustrates a possible reaction pathway for formation of two disulfide bonds sequentially between a pair of protected thiol side chains "$SR_1$" and then between a pair of thiol side chains "$SR_2$". For the sequential formation of the two disulfide bonds, a reaction mixture containing synthesized peptides incorporating cysteine residues having pairs of $SR_1$ and $SR_2$ is heated first to about 60° C. to effect deprotection of the pair of $SR_1$ and form a disulfide bond therebetween. Then the temperature is raised to 100° C. to do the same with the two $SR_2$.

Figure 3:
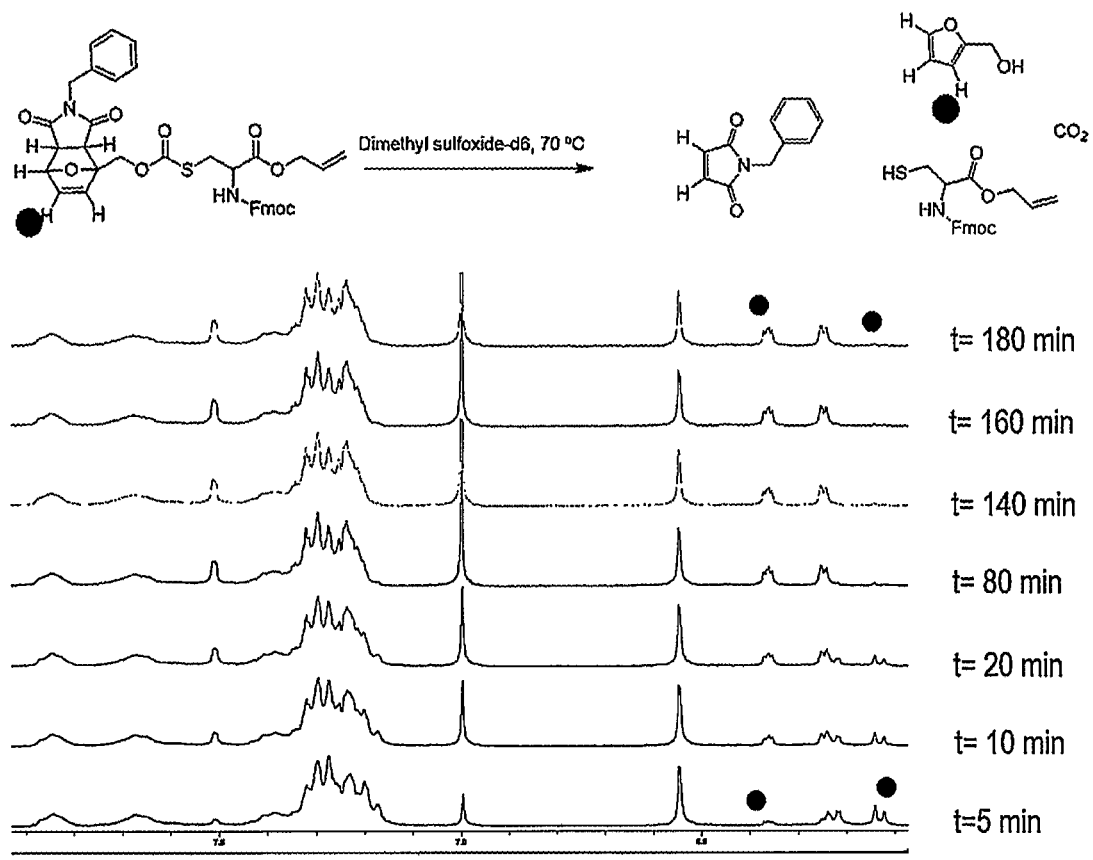
FIG. 3 shows on the upper end, the example of a reverse Diels-Alder reaction for compound 188, and on the lower end a series of $^1$H NMR spectra taken of an initial sample of compound 188 after specific timepoints (selected timepoints only). Specific protons in the starting material and furna product are highlighted; the relative integration of the two indicated signals can be used to quantify the conversion of the reaction. This was cross-checked with three other signals and all measurements give the same values of conversion.

Reference is made to FIG. 3 which demonstrates that at XXX ° C. the endcap is essentially completely removed from the cysteine in YYY minutes and that this change can be readily monitored by nuclear magnetic resonance.

Figure 4:
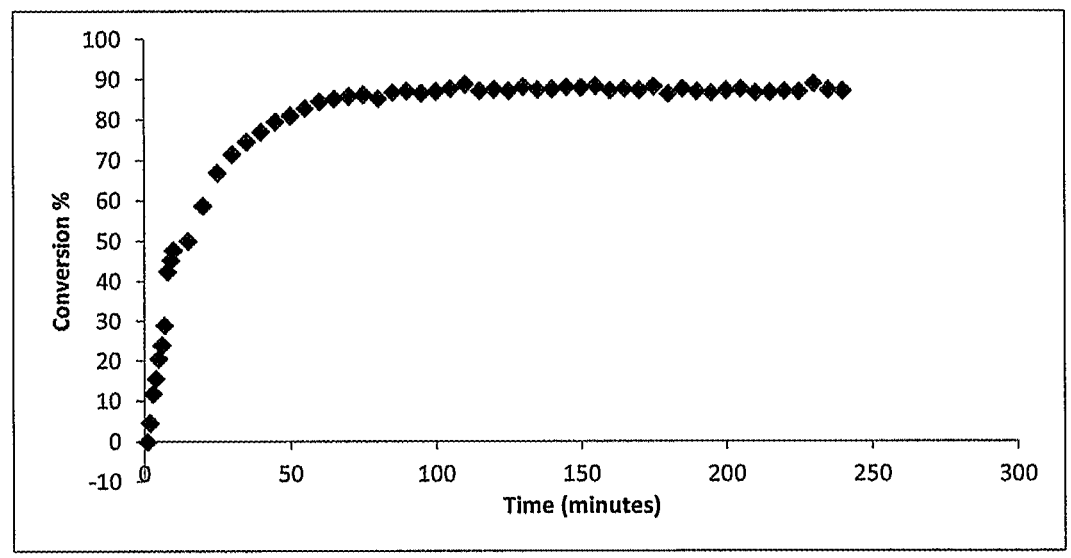
FIG. 4 shows a deprotection curve showing release of a preferred protecting group from a protected cysteine residue 188, with the Y-axis represents the percent release of the cysteine and the X-axis represents the time in minutes. The Y values do not reach 100% due to the high concentration of the experiment, and the restoration of the cyloadduct following release. Reaction is essentially complete after 40 minutes. This figure corresponds to the experimental series provided in FIG. 3.

Reference is made to FIG. 4 which demonstrates a typical experiment, like that in FIG. 3, showing the end-cap removal and release of free cysteine as a function of time. This particular example relates to the spectra provided in FIG. 3, compound 188 releasing the end-cap at YYY ° C.

In another preferred embodiment, there is provided a thermally-sensitive protecting group provided with a cycloadduct of a S-substituted furfural alcohol and an N-alkyl or N-aryl-substituted maleimide, and which may be configured to permit different thermal sensitive triggers from 40° C. to 120° C., and which may permit attachment to a protected cysteine amino acid for a solid-phase synthesis, such as Fmoc solid-phase synthesis. Again, heat may be an ideal trigger for selective deprotection and disulfide bond formation, without necessarily requiring use of a reagent, and which may be applicable to conditions with a greater dynamic range, lower background cleavage under standard operations, and reduced interference with ideal reaction conditions for disulfide bond formation.

Preferably, the protecting group is compound having structural formula 1 or 2 as shown below:

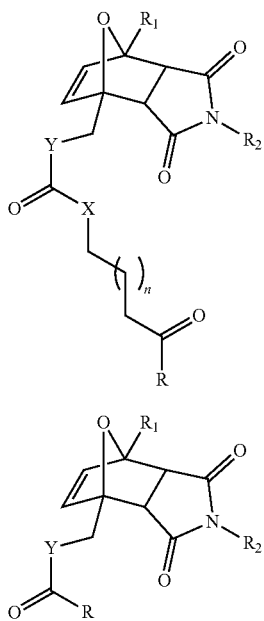

wherein R is an activated ester or acid or forms part thereof; X is sulfur, oxygen or nitrogen; Y is oxygen or sulfur; $R_1$ and $R_2$ are alkyl, aryl, a halogen, an ether, a thioether, a dialkylamine, trialkylammonium, an ester or an acid derivative thereof, or a ketone; and n is an integer from 1 to 9. It is to be appreciated that compound 2 is provided without a linker included with compound 1 for direct attachment to a cysteine residue.

Compounds 1 and 2 were made through the Diels-Alder reaction between the appropriate hydroxymethyl furan and maleimide using temperatures of reaction between 0 and 90° C., and solvents, such as benzene, acetonitrile, chloroform, dichloromethane, tetrahydrofuran, DMSO, DMF, toluene, xylene, hydrocarbon solvents, dichloroethane, tetrachloroethane, dioxane, methanol and/or isopropanol with a reaction times between 15 minutes and 48 hours. The endo and exo cycloadducts were separated using column chromatography, HPLC or crystallization from an appropriate solvent.

The group Y was then activated using a carbonate equivalent agent to make a chloroformate or activated carbonate. Preferred reagents include phosgene, diphosgene, triphosgene, 4-nitrophenylchlorofornate, carbonyl diimidazole and others alike. The foregoing steps could provide for the active protecting group precursor 2.

In one embodiment, the activated carbonate thus obtained was then treated with an alkyl linker with both ends of the chain functionalized—one with a nucleophilic heteroatom (amine, hydroxyl or thiol) and the other with a carboxylic acid or protected carboxylic acid, or masked carboxylic acid. The number of methylene groups or substituted methylene groups between the two terminal functionalities may be 3 to 10, inclusive.

Alternatively, the activated carbonate derivative of the chloroformate was not further functionalized, in which case the activated carbonate was used directly with the cysteine residue.

General Procedures and Materials

Solvents were purchased from Caledon Labs (Caledon, Ontario), Sigma-Aldrich (Oakville, Ontario) or VWR Canada (Mississauga, Ontario). Other chemicals were purchased from Sigma-Aldrich, AK Scientific, Oakwood Chemicals. Alfa Aesar or Acros Chemicals and were used without further purification unless otherwise noted.

Anhydrous toluene, tetrahydrofuran (THF), diethyl ether and N,N-dimethylformamide (DMF) were obtained from an Innovative Technology (Newburyport, USA) solvent purification system based on aluminium oxide columns. $CH_2Cl_2$, pyridine, acetonitrile, N,N-diisopropylethylamine (DIPEA) and $NEt_3$ were freshly distilled from $CaH_2$ prior to use. Purified water was obtained from a Millipore deionization system. All heated reactions were conducted using oil baths on IKA RET Basic stir plates equipped with a P1000 temperature probe. Thin layer chromatography was performed using EMD aluminum-backed silica 60 F254-coated plates and were visualized using either UV-light (254 nm), $KMnO_4$, vanillin, Hanessian's stain, or Dragendorff's stain. Preparative TLC was done using glass-backed silica plates (Silicycle) of either 250, 500, 1000 or 2000 μm thickness depending on application. Column chromatography was carried out using standard flash technique with silica (Siliaflash-P60, 230-400 mesh Silicycle) under compressed air pressure. Standard work-up procedure for all reactions undergoing an aqueous wash involved back extraction of every aqueous phase, a drying of the combined organic phases with anhydrous magnesium sulphate, filtration either using vacuum and a sintered-glass frit or through a glasswool plug using gravity, and concentration under reduced pressure on a rotary evaporator (Buchi or Synthware). $^1$H NMR spectra were obtained at 300 MHz or 500 MHz, and $^{13}$C NMR spectra were obtained at 75 or 125 MHz on Bruker instruments. NMR chemical shifts (δ) are reported in ppm and are calibrated against residual solvent signals of $CHCl_3$ (δ 7.26), DMSO-$d_6$ (δ 2.50), acetone-$d_5$ (δ 2.05), or methanol-$d_3$ (δ 3.31). HRMS were conducted on a Waters XEVO G2-XS TOF instrument with an ASAP probe in CI mode. Peptide synthesis was accomplished using a modified Focus XC-6RV from AAPPTEC controlled by a PC loaded with Focus-XC software. Lyophilization was accomplished using a Sharp Freeze −80° C./6 L lyophilizer from AAPPTEC equipped with a 10-sample manifold. HPLC purification was conducted using analytical analysis on either a Waters HPLC with a 2489 UV/Vis detector and 1525 Binary HPLC pump; or a Varian ProStar UIPLC equipped with two 218 pumps, a 320 UV detector, 330 photodiode array detector, 351 RI detector, and a 410 autosampler. Preparative HPLC was conducted using an Interchim puriFlash 5.25 multi HPLC with four individual solvent pumps.

Synthesis of Cycloadducts:

General Procedure for the Synthesis of Maleamic Acids 5a, 6a, 7a:

All compounds, or namely N-(4-methoxyphenyl) maleamic acid 5a, N-(4-nitrophenyl)maleamic acid 6a and N-benzylmaleamic acid 7a were synthesized using methodologies described in Sortino, M. et al., N-Phenyl and N-phenylalkyl-maleimides acting against *Candida* spp.: Time-to-kill, stability, interaction with maleamic acids. *Bioorgan. Med. Chem.* 2008, 16 (1), 560-568. DOI: http://dx.doi.org/10.1016/j.bmc.2007.08.030, the entire content of which is incorporated herein by reference, with yields ranging from 90% to 91%. Briefly, maleic anhydride (S1) (500 mg, 5.2 mmol) and equimolar amounts of the required amine were combined in $CHCl_3$ (6 mL) and stirred for 45 minutes as a precipitate formed. This precipitate was then filtered and washed with cold (4° C.) water. The analytical data for these maleamic acids have been previously published, and the data was consistent with the published spectra, as shown in Sortino noted above and in Sortino, M. et al., Antifungal, cytotoxic and SAR studies of a series of N-alkyl, N-aryl and N-alkylphenyl-1,4-pyrrolediones and related compounds. *Bioorgan. Med. Chem.* 2011, 19 (9), 2823-2834. DOI: http://dx.doi.org/0.1016/j.bmc. 2011.03.038, the entire content of which is incorporated herein by reference.

General Procedure for Synthesis of Maleimides 5, 6 and 7:

The maleamic acids (5a, 6a or 7a, 4.7 mmol) were dissolved in 5 mL of acetic anhydride along with sodium acetate (100 mg, 1.2 mmol). The mixture was heated for 2-4 h at 100° C. (exact reaction time depended on the substituent), until the reaction was determined to be complete by TLC. The solution was then cooled, diluted with water, then extracted repeatedly with ethyl acetate. The combined organics were dried with magnesium sulfate, and filtered and concentrated in the usual fashion. The solid residue was then redissolved in a minimum amount of THF, and precipitated through the dropwise addition of ice-cold ether. The solid was recovered, resuspended in additional minimal THF, and precipitated by addition into cold water. A final filtration provided the desired maleimides in 73% to 80% yield. Spectroscopic data is consistent with previous reports, as noted in Sortino, M. et al., Antifungal, cytotoxic and SAR studies of a series of N-alkyl, N-aryl and N-alkylphenyl-1, 4-pyrrolediones and related compounds. *Bioorgan. Med. Chem.* 2011, 19 (9), 2823-2834. DOI: http://dx.doi.org/10.1016/j.bmc. 2011.03.038.

N-benzyl-Maleimide 7

Prepared as per the general procedure above using 1 g of maleic anhydride (2-fold scale of the general protocol). Synthesis of 7a proceeded for 45 minutes, providing the maleimic acid in 93% crude yield; the ring closing to 7 required only 1 hour. The crude mixture was first purified by flash chromatography (7:3 hexanes-ethyl acetate), and the fractions containing the product were combined, concentrated, and then recrystallized from 2-propanol and water to provide an 80% yield of the title compound, as white crystals in 75% overall yield after vacuum drying.

White crystals. $^1$H NMR (300 MHz, CDCl$_3$) $\delta_{ppm}$: 7.33-7.22 (5H, m), 6.69 (2H, s), 4.66 (2H, s). Spectral data are consistent with previously published spectra in Sortino, M. et al., N-Phenyl and N-phenylalkyl-maleimides acting against *Candida* spp.: Time-to-kill, stability, interaction with maleamic acids. *Bioorgan. Med. Chem.* 2008, 16 (1), 560-568. DOI: http://dx.doi.org/10.1016/j.bmc.2007.08.030.

N-(p-methoxyphenyl)-Maleimide 5

Prepared as per the general procedure above using 12.0 g of maleic anhydride (12-fold scale of the general protocol). Synthesis of 5a proceeded for 45 minutes, providing the maleimic acid in 90% crude yield as a yellow powder. The ring closing (using 130 mL of acetic anhydride and 5.8 g of sodium acetate) provided a dark yellow amorphous solid, that after recrystallization as in the general protocol, was recovered as bright yellow needles in 73% yield: 66% yield overall from the maleic anhydride.

Yellow needles. $^1$H NMR (300 MHz, CDCl$_3$) $\delta_{ppm}$: 7.27-7.23 (m, 2H), 7.03-6.98 (m, 2H), 6.85 (s, 2H), 3.80 (s, 3H). Spectral data are consistent with previously published spectra in Lee, H. S. et al., Substituent chemical shifts of N-arylsuccinanilic acids, N-arylsuccinimides, N-arylmaleanilic acids, and N-arylmaleimides. *Magn. Reson. Chem.* 2009, 47 (9), 711-715. DOI: 10.1002/mrc.2450, the entire content of which is incorporated herein by reference.

N-(p-nitrophenyl)-Maleimide 6

Prepared as per the general procedure above using 10.0 g of maleic anhydride (10-fold scale of the general protocol). Synthesis of 6a proceeded for 2 hours, providing the maleimic acid in 91% crude yield as brown crystals. The ring closing (using 115 mL of acetic anhydride and 5.1 g of sodium acetate) provided a dark yellow amorphous solid, that after recrystallization as in the general protocol, was recovered as a pale yellow powder in 78% yield; 71% yield overall from the maleic anhydride.

Yellow powder, $^1$H NMR (300 MHz, CDCl$_3$) $\delta_{ppm}$: 8.35-8.32 (m, 2H), 7.70-7.60 (m, 2H,), 6.94 (s, 2H). Spectral data are consistent with previously published spectra in Lee, H. S. et al., Substituent chemical shifts of N-arylsuccinanilic acids, N-arylsuccinimides, N-arylmaleanilic acids, and N-arylmaleimides. *Magn. Reson. Chem.* 2009, 47 (9), 711-715. DOI: 10.1002/mrc.2450.

5-Nitrofurfural Diacetate, S3

Prepared according to a modified version of the protocol noted in Jin. H. et al., Lead optimization and anti-plant pathogenic fungi activities of daphneolone analogues from *Stellera chamaejasme* L. *Pestic. Biochem. Physiol.* 2009, 93 (3), 133-137. DOI: https://doi.org/10.1016/j.pestbp.2009.01.002, the entire content of which is incorporated herein by reference. A mixture of 8.6 mL concentrated HNO$_3$ and 0.06 mL concentrated H$_2$SO$_4$ was slowly added into 90 mL of acetic anhydride while stirring at a temperature of 0° C. This was followed by the slow addition of 10.4 mL of furfural, S2, into the acid mixture with stirring and temperature remaining at 0° C. The mixture was left to stir at this same temperature for 1 hour. At this time, 80 mL of water was added and the mixture was left to stir at room temperature for an additional 30 minutes, over which time a white precipitate formed. A 10% NaOH solution (10 g of NaOH in 100 mL of water) was then added to the mixture until the pH rose to 2.5. The mixture was then heated in a water bath at 55° C. for 1 hour. After cooling, the precipitate was filtered and washed with water prior to being recrystallized from anhydrous ethanol and dried to provide 5.2 g of white crystals in a 75% yield. The material was then used without further purification. R$_f$=0.37 (6:4, hexanes-ethyl acetate).

5-Nitrofurfural, S4

Prepared according to a modified version of the protocol noted in Jin, H. et al., Lead optimization and anti-plant pathogenic fungi activities of daphneolone analogues from *Stellera chamaejasme* L. *Pestic. Biochem. Physiol.* 2009, 93 (3), 133-137. DOI: https://doi.org/10.1016/j.pestbp.2009.01.002. Previously prepared 5-nitrofufural diacetate (S3, 5.2 g, 21.4 mmol) was added to 52 mL of 50% H$_2$SO$_4$ and the resulting mixture was heated using a heat gun (Wagner model #283022 HT 775, 540° C.) for 2 minutes. After cooling, the hydrolysate was extracted via ethyl acetate and the organic layer was washed with water, dried with magnesium sulfate and then filtered and concentrated. A simple distillation provided, after cooling of the distillate, 2.5 g of the title compounds, S4, as a yellow-brownish solid in 83% yield.

Yellow-brownish solid; R$_f$=0.43 (1:1, hexanes-ethyl acetate); $^1$H NMR (300 MHz, CDCl$_3$) $\delta_{ppm}$: 9.85 (s, 1H), 7.43 (d, J=3.82 Hz, 1H), 7.36 (d, J=3.87 Hz, 1H). These obtained values are in agreement with previously reported spectroscopic data noted in Natarajan, P. et al., Silver(I)-Promoted ipso-Nitration of Carboxylic Acids by Nitronium Tetrafluoroborate. *J. Org. Chem.* 2015, 80 (21), 10498-10504. DOI: 10.1021/acs.joc.5b02133, the entire content of which is incorporated herein by reference.

5-Nitro-2-furanmethanol, 2

Prepared according to a modified version of the protocol of noted in Emami, S. et al., 7-Piperazinylquinolones with methylene-bridged nitrofuran scaffold as new antibacterial agents. *Med. Chem. Res.* 2013, 22 (12), 5940-5947. DOI: 10.1007/s00044-013-0581-9, the entire content of which is incorporated herein by reference. 5-nitrofurfural (S4, 2.22 g, 15.7 mmol) was dissolved in 47 mL of absolute methanol and the solution was cooled to 0° C. Then $NaBH_4$ (0.65 g, 0.017 mol) was slowly added and the solution was stirred for another 30 minutes. Once the reaction was complete, the solvent was removed under reduced pressure and the residue was then dissolved in a minimum amount of water. This solution was extracted with diethyl ether (3×10 mL). The combined organic phases were then washed with water, dried with magnesium sulfate, filtered and concentrated. This provided 0.78 g of the title compound as a yellow oil in a moderate 35% yield.

Yellow oil; $R_f$=0.38 (1:1, hexanes-ethyl acetate); $^1$H NMR (300 MHz, $CDCl_3$) $\delta_{ppm}$: 7.28 (1H, d, J=3.71), 6.55 (1H, d, J=3.58), 4.70 (2H, s), 2.68 (1H, bs). These obtained values are in agreement with previously reported spectroscopic data noted in Berry, J. M. et al., 5-Nitrofuran-2-ylmethyl group as a potential bioreductively activated pro-drug system. *J. Chem. Sc. Perkin. Trans.* 1 1997. (8), 1147-1156. DOI: 10.1039/a607202j, the entire content of which is incorporated herein by reference.

Methyl 5-bromo-2-furoate S6

Prepared according to the approach noted in Torii, S. et al., Anodic Reaction of 2-Furoic Acids. II. Electrolysis of Methyl 5-Acetyl-2-furoate and Its Homologous in Protic Solvents. *Bull. Chem. Soc. Jpn.* 1972, 45 (9), 2783-2787. DOI: 10.1246/bcsj.45.2783, the entire content of which is incorporated herein by reference. Bromine (6.07 g, 0.038 mol) was carefully added (dropwise over a period of 15 minutes) to a solution of methyl furoate (S5, 3.2 g, 0.025 mol) stirred at 50° C. under an argon atmosphere in a flame-dried round-bottom flask. The resulting dark orange/brownish solution was additionally stirred for another 15 minutes at 50° C. The reaction mixture was then poured into cold water (10 mL) and extracted with ethyl acetate (2×50 mL). The combined extracts were washed with water (1×10 mL) and brine (1×10 mL) prior to being dried with magnesium sulfate and concentrated. The final product was purified by flash chromatography (10:1, hexanes-ethyl acetate) to obtain 4.5 g of S6 in 85% yield. The spectral data was consistent with literature reports as noted in Torii above. $R_f$=0.17 (7:3, hexanes-ethyl acetate).

5-Bromo-2-Furanmethanol 3

Prepared according to a modified version of the approach noted in Bi, J. et al., Application of furyl-stabilized sulfur ylides to a concise synthesis of 8a-epi-swainsonine. *Chem. Commun.* 2008, (1), 120-122. DOI: 10.1039/b713447a, the entire content of which is incorporated herein by reference. A stirred solution of methyl 5-bromo-2-furoate (S6, 6.7 g, 4.6 mmol) in anhydrous THF (111 mL) was cooled to 0° C. $LiAlH_4$ (1.4 g, 5.1 mmol) was carefully added to the reaction mixture, which was then stirred for a period of 15 minutes. Then, the reaction mixture was warmed to room temperature over a period of 45 minutes prior to a standard Fieser quench and filtration (see (a) Fieser, L. F. et al., *Reagents for Organic Synthesis*. Wiley: New York, 1976; p 1140: (b) Amundsen, L. H. et al., Reduction of Nitriles to Primary Amines with Lithium Aluminum Hydridel. *J. Am. Chem. Soc.* 1951, 73 (1), 242-244. DOI: 10.1021/ja01145a082, the entire contents of both of which are incorporated herein by reference); the THF was mostly removed via rotary evaporation. The resulting crude was diluted with ethyl acetate (200 mL) and washed with water (50 mL) and brine (50 mL). It was then dried over magnesium sulfate and concentrated and the final product, 3.9 g of a colorless oil, was obtained after flash chromatography (5:1, hexanes-ethyl acetate) in 65% yield. Spectral data is consistent with the published data, as noted in Bi above. $R_f$=0.50 (8:2, hexanes-ethyl acetate).

Methyl 5-methoxy-2-furoate S7

Prepared according to a modified version of the protocol of Torii, S. et al., Anodic Reaction of 2-Furoic Acids. II. Electrolysis of Methyl 5-Acetyl-2-furoate and Its Homologous in Protic Solvents. *Bull. Chem. Soc. Jpn.* 1972, 45 (9), 2783-2787. DOI: 10.1246/bcsj.45.2783. Methyl 5-bromo-2-furoate (S6, 2.2 g, 10.7 mmol) was added to a solution of sodium (0.6 g) and sodium iodide (0.03 g) in 30 ml of absolute methanol. The solution was refluxed for 7 hours, then poured into cold water (100 mL). The mixture was then extracted thrice with diethyl ether, and the combined organics were dried over magnesium sulfate, filtered and concentrated. Chromatography of the resulting residue (8:2, hexanes-ethyl acetate) provided 0.8 g of the title compound as an oily product in 48% yield.

Clear oil; $R_f$=0.50 (8:2, hexanes-ethyl acetate); $^1$H NMR (300 MHz, $CDCl_3$) $\delta_{ppm}$: 7.13 (d, J=3.69 Hz, 1H), 5.33 (d, J=3.60 Hz, 1H), 3.96 (s, 3H), 3.86 (s, 3H). Spectral data is in agreement with published data noted in Schwartz, D. A. et al., Synthetic approaches to haplophytine. 2. Synthesis of 4-methylamino-1-(2-furanyl)-2-phenyl-2-(2-pivaloylamidophenyl)butan-1-one. *Can. J. Chem.* 1983, 61 (6), 1126-1131. DOI: 10.1139/v83-201, the entire content of which is incorporated herein by reference.

5-methoxy-2-furanmethanol 4

Prepared according to a modified version of the protocol noted in Manly, D. G. et al., Simple Furan Ethers. II: 2-Alkoxy- and 2-Aryloxy-furans. *J. Org. Chem.* 1956, 21 (5), 516-519. DOI: 10.1021/jo01111a008, the entire content of which is incorporated herein by reference. A solution of methyl 5-methoxy-2-furoate (S7, 0.45 g) in 2 mL of dry ether was slowly added to a fast-stirring solution of $LiAlH_4$ (0.14 g) in 4.5 mL of dry ether. After a 1.5 hour reflux, 0.3 mL of water was carefully added prior to 1.9 mL of sodium hydroxide. The reaction mixture was diluted with ether, and the phases separated. The aqueous layer was then extracted several times with ether, and the combined ether extracts were dried and evaporated to provide 150 mg of the title compound as a colorless liquid in 40% yield. No further purification was required. Colourless oil; $R_f$=0.21 (3:7, hexanes-ethyl acetate); $^1$H NMR (300 MHz, $CDCl_3$) $\delta_{ppm}$: 6.09 (d, J=3.30 Hz, 1H), 5.03 (d, J=3.30 Hz, 1H), 4.37 (s, 21H), 3.78 (s, 3H), 2.89 (bs, 1H). Spectral data is in agreement with published data noted in Schwartz, D. A. et al., Synthetic approaches to haplophytine. 2. Synthesis of 4-methylamino-1-(2-furanyl)-2-phenyl-2-(2-pivaloylamidophenyl)butan-1-one. *Can. J. Chem.* 1983, 61 (6), 1126-1131. DOI: 10.1139/v83-201.

rac-(3aR,4R,7S,7aS)-4-(hydroxymethyl)-2-(4-methoxyphenyl)-3a,4,7,7a-tetrahydro-1H-4,7-epoxyisoindole-1,3(2H)-dione ($15_{endo}$) and rac-(3aS,4R,7S,7aR)-4-(hydroxymethyl)-2-(4-methoxyphenyl)-3a,4,7,7a-tetrahydro-1H-4,7-epoxyisoindole-1,3(2H)-dione ($15_{exo}$)

N-(p-methoxyphenyl)-Maleimide 5 (0.5 g, 2.67 mmol) and 2-(hydroxymethyl) furan 1 (0.31 g, 3.2 mmol) were dissolved in anhydrous acetonitrile under a nitrogen atmosphere in a flame-dried flask equipped with a magnetic stirring-bar. The reaction was stirred at 35° C. for 18 hours. When TLC indicated there was no longer starting material present, the solvent was removed, and the reaction was concentrated under reduced pressure for 1 hour. Endo and exo cycloadducts was separated by column (6:4 to 4:6, hexanes-ethyl acetate). We obtained two fractions, one contained 690 mg of pure endo material (85% yield), while the second (<5%) contained 26 mg of a mixture of the exo and endo isomers. Because these compounds have an inherently unstable nature at ambient temperatures, they are kept stored at −20° C. until required.

rac-(3aR,4R,7S,7aS)-4-(hydroxymethyl)-2-(4-methoxyphenyl)-3a,4,7,7a-tetrahydro-1H-4,7-epoxyisoindole-1,3(2H)-dione ($15_{endo}$)

$R_f$=0.30 (2:8, hexanes-ethyl acetate); $^1$H NMR (300 MHz, CD$_3$CN): $\delta_{ppm}$ 7.17-7.12 (m, 4H), 6.71 (dd, J=5.0, 1.5 Hz, 1H), 6.62 (dd, J=5.8, 1.6 Hz, 1H), 5.45 (d, J=6.7 Hz, 1H), 4.32 (dd, J=12.94, 5.67 Hz, 1H), 4.20 (dd, J=12.82, 6.37 Hz, 1H), 3.95 (s, 3H), 3.93-3.85 (m, 1H), 3.66 (d, J=7.67 Hz, 1H), 3.31 (t, J=5.88 Hz, 1H, OH); $^{13}$C NMR (75 MHz, CD$_3$CN): $\delta_{ppm}$ 175.0, 174.7, 159.7, 135.7, 135.4, 128.0, 124.9, 114.0, 92.7, 79.5, 60.5, 55.3, 48.1, 45.7; HRMS (CI): Calculated for [M]$^+$ (C$_{16}$H$_{15}$NO$_5$): 301.0950. Found: 301.0944.

rac-(3aS,4R,7S,7a R)-4-(hydroxymethyl)-2-(4-methoxyphenyl)-3a,4,7,7a-tetrahydro-1H-4,7-epoxyisoindole-1,3(2H)-dione ($15_{exo}$)

$R_f$=0.19 (1:9, hexanes-ethyl acetate); $^1$H NMR (300 MHz, CDCl$_3$): $\delta_{ppm}$ 7.07-6.89 (m, 4H), 6.65 (d, J=5.71 Hz, 1H), 6.60-6.55 (m, 1H), 5.36 (d, J=1.65 Hz, 1H), 4.17-4.12 (m, 2H), 3.82 (s, 3H), 3.13 (d, J=6.57 Hz, 1H), 3.09 (d, J=6.58 Hz, 1H), 2.84 (bs, 1H, OH).

rac-(3aR,4R,7S,7aS)-4-(hydroxymethyl)-2-(4-nitrophenyl)-3a,4,7,7a-tetrahydro-1H-4,7-epoxyisoindole-1,3(2H)-dione ($16_{endo}$) and rac-(3aS,4R,7S,7aR)-4-(hydroxymethyl)-2-(4-nitrophenyl)-3a,4,7,7a-tetrahydro-1H-4,7-epoxyisoindole-1,3(2H)-dione ($16_{exo}$)

N-(p-nitrophenyl)-Maleimide 6 (0.5 g, 2.30 mmol) and 2-(hydroxymethyl) furan 1 (0.273 g, 2.80 mmol) were dissolved in anhydrous acetonitrile under a nitrogen atmosphere in a flame-dried flask equipped with a magnetic stirring-bar. The reaction was stirred at 40° C. After 4.5 hours, a new polar spot formed but starting material was still present and the reaction was left to stir at the same temperature overnight. When TLC indicated there was no longer starting material present, the solvent was removed, and the reaction was concentrated under reduced pressure. A column with (7:3 to 3:7, hexanes-ethyl acetate) was used to separate the components. The pure endo product was separated (100 mg, 13%), while a mixture of the endo and exo products (300 mg, 39% yield) was obtained in a second fraction. Ultimately, there was a yield of 52% endo/exo cycloadduct mixture. Since this mixture has an inherently unstable nature at ambient temperatures, it is kept stored at −20° C. until required.

rac-(3aR,4R,7S,7aS)-4-(hydroxymethyl)-2-(4-nitrophenyl)-3a,4,7,7a-tetrahydro-1H-4,7-epoxyisoindole-1,3(2H)-dione ($16_{endo}$)

Light yellow solid; $R_f$=0.30 (3:7, hexanes-ethyl acetate): $^1$H NMR (300 MHz, CD$_3$CN): 8.29 (d, J=8.62 Hz, 2H), 7.42 (d, J=8.60 Hz, 2H), 6.60 (d, J=5.76 Hz, 1H), 6.49 (d, J=5.69 Hz, 1H), 5.34 (d, J=5.50 Hz, 1H), 4.18 (dd, J=12.90, 5.80 Hz, 1H), 4.06 (dd, J=12.89, 6.30 Hz, 1H), 3.81 (dd, J=7.60, 5.61 Hz, 1H), 3.59 (d, J=7.75 Hz, 1H), 3.24 (t, J=6.08 Hz, 1H, OH); $^{13}$C NMR (75 MHz, CDCl$_3$): $\delta_{ppm}$ 174.1, 173.8, 147.4, 137.6, 135.8, 135.6, 127.7, 124.4, 92.9, 79.6, 60.3, 48.3, 45.9; HRMS (CI): Calculated for [M]$^+$ (C$_{15}$H$_{12}$N$_2$O$_6$): 316.0695. Found: [M]$^+$ 316.0697.

rac-(3aS,4R,7S,7aR)-4-(hydroxymethyl)-2-(4-nitrophenyl)-3a,4,7,7a-tetrahydro-1H-4,7-epoxyisoindole-1,3(2H)-dione ($16_{exo}$)

White creamy solid; $R_f$=0.25 (3:7, hexanes-ethyl acetate); $^1$H NMR (300 MHz, CDCl$_3$): $\delta_{ppm}$ 8.32 (d, J=9.16 Hz, 2H), 7.58 (d, J=9.05 Hz, 2H), 6.67-6.60 (m, 2H), 5.43 (d, J=1.22 Hz, 1H), 4.19 (d, J=7.29 Hz, 2H), 3.24 (d, J=6.53 Hz, 1H), 3.19 (d, J=6.70 Hz, 1H), 2.54 (t, J=7.21 Hz, 1H, OH)

rac-(3aR,4R,7S,7aS)-2-benzyl-4-(hydroxymethyl)-3a,4,7,7a-tetrahydro-1H-4,7-epoxyisoindole-1,3(2H)-dione ($17_{endo}$) and rac-(3aS,4R,7S,7aR)-2-benzyl-4-(hydroxymethyl)-3a,4,7,7a-tetrahydro-1H-4,7-epoxyisoindole-1,3(2H)-dione ($17_{exo}$)

Made according to the protocol as noted in Fan, B. et al, Thermo-responsive self-immolative nanoassemblies: Direct and indirect triggering. Chem. Commun. 2017, 0, 12068-12071. DOI: http://dx.doi.org/10.1039/c7cc06410a, the entire content of which is incorporated herein by reference. N-benzyl maleimide (7, 2.0 g, 10.7 mmol) (see Sortino, M. et al., N-Phenyl and N-phenylalkyl-maleimides acting against *Candida* spp.: Time-to-kill, stability, interaction with maleamic acids. *Bioorgan. Med. Chem.* 2008, 16 (1), 560-568. DOI: http://dx.doi.org/10.1016/j.bmc.2007.08.030) and 2-(hydroxymethyl) furan (1, 931 μL, 1.05 g, 10.7 mmol) were dissolved in anhydrous acetonitrile under a nitrogen atmosphere in a flame-dried flask equipped with a magnetic stirring-bar. The reaction was stirred at 35° C. for 14 hours. When TLC indicated the reaction had reached equilibrium, the solvent was removed, and the reaction was concentrated under reduced pressure for 1 hour. Crude NMR indicated a ratio of (1:0.4:0.3) of endo-exo-unreacted maleimide. The crude material was then purified by flash chromatography (6:4 to 4:6, hexanes-ethyl acetate) to provide 1.61 g (53% yield) of the endo and 677 mg (22% yield) of the exo product for a combined 75% isolated yield. Due to the inherent thermal instability, the material is stored at −20° C. until needed.

rac-(3aR,4R,7S,7aS)-2-benzyl-4-(hydroxymethyl)-3a,4,7,7a-tetrahydro-1H-4,7-epoxyisoindole-1,3(2H)-dione ($17_{endo}$)

Clear oil; $R_f$=0.27 (6:4, hexanes-ethyl acetate); $^1$H NMR (300 MHz, CDCl$_3$): $\delta_{ppm}$ 7.31-7.26 (m, 5H), 6.15 (dd, J=5.8, 1.5 Hz, 1H), 6.06 (d, J=5.8 Hz, 1H), 5.26 (dd, J=5.5, 1.6 Hz, 1H), 4.47 (s, 2H), 4.25 (d, J=12.2 Hz, 1H), 4.15 (d, J=12.2 Hz, 1H), 3.63 (dd, J=7.6, 5.5 Hz, 1H), 3.40 (d, J=7.6 Hz, 1H), 2.11 (s, 1H). Spectral data is consistent with the published data noted in Fan, B. et al, Thermo-responsive self-immolative nanoassemblies: Direct and indirect triggering. *Chem. Commun.* 2017, 0, 12068-12071. DOI: http://dx.doi.org/10.1039/c7cc06410a.

rac-(3aS,4R,7S,7aR)-2-benzyl-4-(hydroxymethyl)-3a,4,7,7a-tetrahydro-1H-4,7-epoxyisoindole-1,3(2H)-dione ($17_{exo}$)

Colourless solid; $R_f$=0.14 (6:4, hexanes-ethyl acetate); $^1$H NMR (300 MHz, CDCl$_3$): $\delta_{ppm}$ 7.33-7.26 (m, 5H), 6.61 (d, J=5.7 Hz, 1H), 6.54 (dd, J=5.7, 1.5 Hz, 1H), 5.28 (d, J=1.7 Hz, 1H), 4.66 (bs, 2H), 4.09 (dd, J=12.2, 8.8 Hz, 1H), 4.03 (dd, J=12.2, 6.3 Hz, 1H), 3.02 (d, J=6.5 Hz, 1H), 2.99 (d, J=6.5 Hz, 1H), 2.76 (bt, J=7.4 Hz, 1H, OH). Spectral data is consistent with the published data noted in Fan. B. et al, Thermo-responsive self-immolative nanoassemblies: Direct and indirect triggering. *Chem. Commun.* 2017, 0, 12068-12071. DOI: http://dx.doi.org/10.1039/c7cc06410a.

rac-(3aR,4R,7R,7aS)-4-(hydroxymethyl)-2-(4-methoxyphenyl)-7-nitro-3a,4,7,7a-tetrahydro-1H-4,7-epoxyisoindole-1,3(2H)-dione (25$_{endo}$) and rac-(3aS,4R,7R,7aR)-4-(hydroxymethyl)-2-(4-methoxyphenyl)-7-nitro-3a,4,7,7a-tetrahydro-1H-4,7-epoxyisoindole-1,3(2H)-dione (25$_{exo}$)

N-(p-methoxyphenyl)-Maleimide 5 (0.349 g, 1.72 mmol) and 5-nitro-2 furanmethanol 2 (0.295 g, 2.06 mmol) were dissolved in anhydrous acetonitrile under a nitrogen atmosphere in a flame-dried flask equipped with a magnetic stirring-bar. The reaction was stirred at 50-75° C. for 8 hours, at which time TLC analysis (3:7, hexanes-ethyl acetate) indicated the formation of a new, polar spot ($R_f$=0.13). The reaction would not proceed to completion, and although we observed a new spot consistent with the endo product form, it was negligible and was never able to be isolated by chromatography. The reaction was stopped by cooling the mixture, and the solvent was removed. Column chromatography (6:4 to 2:8 to 0.5:9.5, hexanes-ethyl acetate) was carried out, and provided 405 mg of the exo product in 63% yield. The material was kept at −20° C. until required.

rac-(3aS,4R,7R,7aR)-4-(hydroxymethyl)-2-(4-methoxyphenyl)-7-nitro-3a,4,7,7a-tetrahydro-1H-4,7-epoxyisoindole-1,3(2H)-dione (25$_{exo}$)

White spongy solid; $R_f$=0.13 (3:7, hexanes-ethyl acetate); $^1$H NMR $^1$H NMR (300 MHz, CDCl$_3$): $\delta_{ppm}$ 7.19 (d, J=9.03 Hz, 2H), 6.98 (d, J=8.98 Hz, 2H), 6.96 (d, J=5.31 Hz, 1H), 6.90 (d, J=5.58 Hz, 1H), 4.22 (d, J=2.65 Hz, 1H), 4.19 (d, J=1.56 Hz, 1H), 3.83 (s, 3H), 3.77 (d, J=6.64 Hz, 1H), 3.42 (d, J=6.64 Hz, 1H), 2.71 (t, J=7.46 Hz, 1H, OH); $^{13}$C NMR (300 MHz, MeOD): $\delta_{ppm}$ 172.8, 171.6, 160.2, 141.5, 134.8, 128.2, 124.7, 114.4, 112.3, 91.8, 59.2, 55.1, 52.6, 50.9. HRMS (CI): Calculated for [M]$^+$ (C$_{16}$H$_{14}$N$_2$O$_7$): 346.0801; [M+H]$^+$ (C$_6$H$_{15}$N$_2$O$_7$): 347.0874. Found [M+H]$^+$: 347.0877.

rac-(3aR,4R,7R,7aS)-4-(hydroxymethyl)-7-nitro-2-(4-nitrophenyl)-3a,4,7,7a-tetrahydro-1H-4,7-epoxyisoindole-1,3(2H)-dione (26$_{endo}$)

N-(p-nitrophenyl)-Maleimide 2 (0.254 g, 1.16 mmol) and 5-nitro-2-furanmethanol 6 (0.200 g, 1.40 mmol) were dissolved in anhydrous acetonitrile under a nitrogen atmosphere in a flame-dried flask equipped with a magnetic stirring-bar. The reaction was stirred at 40° C. for 4 hours, then at 60° C. for an additional 4 hours, at which point only starting material was observed by TLC (3:7, hexanes-ethyl acetate). The temperature was accordingly increased to 80° C., and was left to stir at this temperature overnight (12 hours). TLC indicated moderate conversion, and the solvent was removed, and the reaction mixture was concentrated. Column purification was then performed (6:4 to 0.5:9.5, hexanes-ethyl acetate). 162 mg of the polar spot was obtained in 31% yield ($R_f$=0.16) and was determined to be exo product. A negligible amount of endo material was observed by crude NMR but was not able to be readily isolated from the starting materials. Product was kept stored at −20° C. until required.

rac-(3aS,4R,7R,7aR)-4-(hydroxymethyl)-7-nitro-2-(4-nitrophenyl)-3a,4,7,7a-tetrahydro-1H-4,7-epoxyisoindole-1,3(2H)-dione (26$_{exo}$)

Off-white spongy solid; $R_f$=0.16 (3:7, hexanes-ethyl acetate); $^1$H NMR (300 MHz, CD$_3$CN): $\delta_{ppm}$ 8.34 (d, J=9.05 Hz, 2H), 7.54 (d, J=9.11 Hz, 2H), 6.93 (d, J=5.73 Hz, 1H), 6.90 (d, J=5.85 Hz, 1H), 4.26 (dd, J=13.21, 6.39 Hz, 1H), 4.05 (dd, J=13.32, 5.80 Hz, 1H), 3.94 (d, J=6.57 Hz, 1H), 3.46 (d, J=6.70 Hz, 1H), 3.44 (t, J=5.93 Hz, 1H, OH); $^{13}$C NMR (100 MHz, CDCl$_3$): $\delta_{ppm}$ 171.7, 170.7, 147.6, 141.3, 137.0, 134.8, 127.5, 124.6, 112.0, 91.7, 59.1, 52.7, 51.0. HRMS (CI): Calculated for [M]$^+$ (C$_{15}$H$_{11}$N$_3$O$_8$): 361.0546; [M+H]$^+$ (C$_{15}$H$_{12}$N$_3$O$_8$): 362.0624. Found [M]$^+$: 362.0614.

rac-(3aR,4R,7R,7aS)-2-benzyl-4-(hydroxymethyl)-7-nitro-3a,4,7,7a-tetrahydro-1H-4,7-epoxyisoindole-1,3(2H)-dione (27$_{endo}$) and rac-(3aS,4R,7R,7aR)-2-benzyl-4-hydroxymethyl)-7-nitro-3a,4,7,7a-tetrahydro-1H-4,7-epoxyisoindole-1,3(2H)-dione (27$_{exo}$)

N-benzyl maleimide 7 (0.322 g, 1.72 mmol) and 5-nitro-2-furanmethanol 2 (0.295 g, 2.06 mmol) were dissolved in anhydrous acetonitrile under a nitrogen atmosphere in a flame-dried flask equipped with a magnetic stirring-bar. The reaction was stirred at 65-70° C. for 16 hours. At that point. TLC analysis (2:8, hexanes-ethyl acetate) showed the formation a new nonpolar spot (endo; $R_f$=0.27) and the formation of a polar spot (exo: $R_f$=0.14). At this point, the reaction was concentrated under reduced pressure, and purified by flash chromatography (3:7 to 1:9, hexanes-ethyl acetate). The first fraction contained 438 mg of product (69% yield) endo product and 129 mg (21% yield) of the exo product. They are both kept stored at −20° C. until required.

rac-(3aR,4R,7R,7aS)-2-benzyl-4-(hydroxymethyl)-7-nitro-3a,4,7,7a-tetrahydro-1H-4,7-epoxyisoindole-1,3(2H)-dione (27$_{endo}$)

White crystal; $R_f$=0.27 (2:8, hexanes-ethyl acetate); $^1$H NMR (300 MHz, CDCl$_3$): $\delta_{ppm}$ 7.35-7.27 (m, 5H), 6.46 (d, J=5.75 Hz, 1H), 6.23 (d, J=5.75 Hz, 1H), 4.55 (d, J=13.96 Hz, 1H), 4.50 (d, J=13.94 Hz, 1H), 4.29 (dd, J=13.13, 6.18 Hz, 1H), 4.19 (dd, J=13.14, 6.94 Hz, 1H), 3.96 (d, J=7.95 Hz, 1H), 3.84 (d, J=7.95 Hz, 1H), 2.16 (t, J=6.60 Hz, 1H, OH); $^{13}$C NMR (300 MHz, CDCl$_3$): $\delta_{ppm}$ 172.6, 170.7, 137.2, 134.9, 132.7, 129.3, 128.8, 128.6, 112.4, 91.7, 60.8, 57.6, 51.0, 48.1, 43.0. HRMS (CI): Calculated for [M]$^+$ (C$_{16}$H$_{14}$N$_2$O$_6$): 330.0852; [M+H]$^+$ (C$_{16}$H$_{15}$N$_2$O$_6$): 331.0930. Found [M+H]$^+$: 331.0939.

rac-(3aS,4R,7R,7aR)-2-benzyl-4-hydroxymethyl-7-nitro-3a,4,7,7a-tetrahydro-1H-4,7-epoxyisoindole-1,3(2H)-dione (27$_{exo}$)

White crystal; $R_f$=0.14 (2:8, hexanes-ethyl acetate); $^1$H NMR (300 MHz, CDCl$_3$): $\delta_{ppm}$ 7.38-7.27 (m, 5H), 6.89 (d, J=5.62 Hz, 1H), 6.83 (d, J=5.52 Hz, 1H), 4.71 (d, J=14.23 Hz, 1), 4.63 (d, J=14.31 Hz, 1H), 4.19-3.99 (m, 21H), 3.64 (d, J=6.48 Hz, 1H), 3.26 (d, J=6.47 Hz, 1H), 2.75-2.68 (m, 1H, OH); $^{13}$C NMR (300 MHz, CDCl$_3$): $\delta_{ppm}$ 173.4, 170.6, 141.3, 135.4, 134.9, 129.1, 128.7, 128.6, 111.4, 9.4, 60.3, 51.7, 50.9, 43.5.

rac-(3aR,4S,7R,7aR)-4-bromo-7-(hydroxymethyl)-2-(4-methoxyphenyl)-3a,4,7,7a-tetrahydro-1H-4,7-epoxyisoindole-1,3(2H)-dione (35$_{endo}$) and rac-(3aS,4S,7R,7aS)-4-bromo-7-(hydroxymethyl)-2-(4-methoxyphenyl)-3a,4,7,7a-tetrahydro-1H-4,7-epoxyisoindole-1.3(2H)-dione (35$_{exo}$)

N-(p-methoxyphenyl)-Maleimide 5 (0.8 g, 3.90 mmol) and 5-Bromo-2-furanmethanol 3 (0.60 g, 3.00 mmol) were dissolved in anhydrous acetonitrile under a nitrogen atmosphere in a flame-dried flask equipped with a magnetic stirring-bar. The reaction was stirred at room temperature for 3 hours, then the progress of reaction was monitored every 2 hours and the temperature was increased from 35° C. to 75° C. over 6 hours, and held at the highest temperature for an additional 10 hours. The reaction was concentrated under reduced pressure and purified by column (6:4 to 2:8, hexanes-ethyl acetate) to separate the starting material from 851 mg of the non-polar endo ($R_f$=0.50, 6:4, hexanes-ethyl acetate) product (61% yield) and 63 mg of a polar exo ($R_f$=0.17, 6:4, hexanes-ethyl acetate) product in <5% yields. The mass balance included some debrominated material, 15 and starting materials. These products kept stored at −20° C. until required.

rac-(3aR,4S,7lR,7aR)-4-bromo-7-(hydroxymethyl)-2-(4-methoxyphenyl)-3a,4,7,7a-tetrahydro-1H-4,7-epoxyisoindole-1,3(2H)-dione (35$_{endo}$)

White solid. R$_f$=0.50 (6:4, hexanes-ethyl acetate); $^1$H NMR (300 MHz, CD$_3$CN): δ$_{ppm}$ 7.06-6.89 (m, 4H), 6.64 (d, J=5.54 Hz, 1H), 6.53 (d, J=5.44 Hz, 1H), 4.14 (dd, J=13.38, 6.13 Hz, 1H), 4.02 (dd, J=12.83, 6.25 Hz, 1H), 3.87 (d, J=7.52 Hz, 1H), 3.79 (s, 3H), 3.74 (d, J=8.01 Hz, 1H), 3.35 (t, J=5.99 Hz, 1H, OH); $^{13}$C NMR (75 MHz, CD$_3$CN): δ$_{ppm}$ 174.9, 174.0, 161.4, 140.9, 138.3, 129.7, 126.0, 115.9, 93.5, 89.8, 61.5, 58.2, 56.8, 46.7. HRMS (CI): Calculated for [M]$^+$ (C$_{16}$H$_{14}$BrNO$_5$): 379.0055. Found: 379.0046.

rac-(3aS,4S,7R,7aS)-4-bromo-7-(hydroxymethyl)-2-(4-methoxyphenyl)-3a,4,7,7a-tetrahydro-1H-4,7-epoxyisoindole-1,3(2H)-dione (35$_{exo}$)

White solid; R$_f$=0.17 (6:4, hexanes-ethyl acetate); $^1$H NMR (300 MHz, CDCl$_3$): δ$_{ppm}$ 7.20 (d, J=8.64 Hz, 1H), 6.97 (d, J=8.67 Hz, 1H), 6.64 (d, J=7.74 Hz, 1H), 6.62 (d, J=7.89 Hz, 1H), 4.01 (d, J=11.56 Hz, 1H), 3.84 (d, J=11.22 Hz, 1H), 3.83 (s, 3H), 3.36-3.33 (m, 2H); $^{13}$C NMR (75 MHz, CDCl$_3$): δ$_{ppm}$ 171.8, 170.5, 159.8, 142.1, 138.7, 127.6, 123.9, 114.5, 89.4, 89.0, 55.5, 54.8, 51.5, 27.4.

rac-(3aR,4S,7R,7aR)-4-bromo-7-(hydroxymethyl)-2-(4-nitrophenyl)-3a,4,7,7a-tetrahydro-1H-4,7-epoxyisoindole-1,3(2H)-dione (36$_{endo}$)

N-(p-nitrophenyl)-Maleimide 6 (990 mg, 5.6 mmol) and 5-Bromo-2-furanmethanol 3 (1.03 g, 4.7 mmol) were dissolved in anhydrous acetonitrile under a nitrogen atmosphere in a flame-dried flask equipped with a magnetic stirring-bar. The reaction was stirred at 50° C. for 72 hours until further conversion was no longer noted by TLC (6:4 hexanes-ethyl acetate). The reaction mixture was concentrated, and the residue purified by column chromatography (6:4, hexanes-ethyl acetate) in two columns successively (the first column provided product contaminated with the starting materials). Crude 1H NMR had shown the presence of both endo and exo derivatives, albeit in low conversion. The small amount of exo was estimated to be well under 3% of the mass balance and was not isolated. The chromatography provided 530 mg of the title compound as a colourless solid in 26% yield.

rac-(3aR,4S,7R,7aR)-4-bromo-7-(hydroxymethyl)-2-(4-nitrophenyl)-3a,4,7,7a-tetrahydro-1H-4,7-epoxyisoindole-1,3(2H)-dione (36$_{endo}$)

White solid; R$_f$=0.20 (6:4, hexanes-ethyl acetate); $^1$H NMR (300 MHz, CDCl$_3$): δ$_{ppm}$ 8.31 (d, J=8.75 Hz, 1H), 7.43 (d, J=8.48 Hz, 1H), 6.65 (d, J=5.46 Hz, 1H), 6.51 (d, J=5.48 Hz, 1H), 4.36 (d, J=12.88 Hz, 1H), 4.24 (d, J=13.02 Hz, 1H), 4.00 (d, J=7.90 Hz, 1H), 3.91 (d, J=8.00 Hz, 1H); $^{13}$C NMR (75 MHz, CDCl$_3$): δ$_{ppm}$ 171.9, 170.7, 147.4, 140.2, 136.0, 127.1, 126.8, 124.6, 91.9, 87.6, 61.0, 56.8, 48.4. HRMS (CI): Calculated for [M]$^+$ (C$_{15}$H$_{11}$BrN$_2$O$_6$): 393.9800, [M+H]$^+$ (C$_{15}$H$_{12}$BrN$_2$O$_6$): 394.9879. Found: 394.9872.

rac-(3aR,4S,7R,7aR)-2-benzyl-4-bromo-7-(hydroxymethyl)-3a,4,7,7a-tetrahydro-1H-4,7-epoxyisoindole-1,3(2H)-dione (37$_{endo}$) and rac-(3aS,4S,7R,7aS)-2-benzyl-4-bromo-7-(hydroxymethyl)-3a,4,7,7a-tetrahydro-1H-4,7-epoxyisoindole-1,3(2H)-dione (37$_{exo}$)

N-benzyl maleimide 7 (0.70 g, 3.8 mmol) and 5 Bromo-2-furanmethanol 3 (0.80 g, 4.5 mmol) were dissolved in anhydrous acetonitrile under a nitrogen atmosphere in a flame-dried flask equipped with a magnetic stirring-bar. The reaction was stirred at room temperature for 7 hours, a TLC (7:3, hexanes-ethyl acetate) showing starting material was left, so the temperature was increased slowly (55'C to 70° C.) and the progress of reaction was monitored every 2 hours. The reaction was left for an additional 14 hours at 70° C. when TLC showed some conversion. The solvent was removed, and the reaction mixture was concentrated. After column chromatography purification of reaction mixture (7:3, hexanes-ethyl acetate), 403 mg of an inseparable mixture of the endo and exo (2:1) cycloadducts as a white solid was obtained with an overall yield of 31%. In none of the more than 10 solvent mixtures examined was separation observed. The mixture was kept stored at −20° C. until required.

rac-(3aR,4S,7R,7aR)-2-benzyl-4-bromo-7-(hydroxymethyl)-3a,4,7,7a-tetrahydro-1H-4,7-epoxyisoindole-1,3(2H)-dione (37$_{endo}$)

R$_f$=0.29 (7:3, hexanes-ethyl acetate); $^1$H NMR (300 MHz, CDCl$_3$): δ$_{ppm}$ 7.37-7.27 (m, 5H), 6.12 (d, J=5.51 Hz, 1H), 5.97 (d, J=5.24 Hz, 1H), 4.52-4.46 (m, 2H), 4.24 (dd, J=12.40, 1.86 Hz, 1H), 4.13 (dd, J=12.44, 2.95 Hz, 1H), 3.79-3.12 (m, 2H), 3.25-3.20 (m, 1H, OH); $^{13}$C NMR (75 MHz, CDCl$_3$): δ$_{ppm}$ 172.9, 172.2, 138.6, 135.2, 135.0, 129.1, 128.6, 128.2, 90.6, 89.1, 68.9, 56.0, 51.6, 47.96, 42.5.

rac-(3aS,4S,7R,7aS)-2-benzyl-4-bromo-7-(hydroxymethyl)-3a,4,7,7a-tetrahydro-1H-4,7-epoxyisoindole-1,3(2H)-dione (37$_{exo}$)

R$_f$=0.28 (7:3, hexanes-ethyl acetate); $^1$H NMR (300 MHz, CDCl$_3$): δ$_{ppm}$ 7.37-7.27 (m, 5H), 6.12 (d, J=5.51 Hz, 1H), 5.97 (d, J=5.24 Hz, 1H), 4.71 (d, J=14.35 Hz, 1H), 4.66 (d, J=14.37 Hz, 1H), 3.93 (d, J=11.41 Hz, 1H), 3.65 (dd, J=14.15, 7.79 Hz, 1H), 3.77-3.73 (m, 1H); 3.25-3.20 (m, 1H, OR); $^{13}$C NMR (75 MHz, CDCl$_3$): δ$_{ppm}$ 172.0, 170.9, 139.2, 135.1, 135.0, 128.7, 128.3, 128.0, 90.5, 88.8, 69.1, 54.8, 48.04, 42.9, 27.3.

Endo/exo mixture HRMS (CI): Calculated for [M]$^+$ (C$_{16}$H$_{14}$BrNO$_4$): 363.0106, [M+H]$^+$ (C$_{16}$H$_{15}$BrNO$_4$): 364.0184. Found: 364.0176.

rac-(3aR,4R,7R,7aS)-4-(hydroxymethyl)-7-methoxy-2-(4-methoxyphenyl)-3a,4,7,7a-tetrahydro-1H-4,7-epoxyisoindole-1,3(2H)-dione (45$_{endo}$) and rac-(3aR,4R,7R,7aS)-4-(hydroxymethyl)-7-methoxy-2-(4-methoxyphenyl)-3a,4,7,7a-tetrahydro-1H-4,7-epoxyisoindole-1,3(2H)-dione (45$_{exo}$)

N-(p-methoxyphenyl)-Maleimide 5 (0.32 g, 2.5 mmol) and 5-methoxy-2-furanmethanol 4 (0.43 g, 2.1 mmol) were dissolved in anhydrous acetonitrile under a nitrogen atmosphere in a flame-dried flask equipped with a magnetic stirring-bar. The reaction was stirred at 45° C. for 4 hours; TLC analysis (2:8, hexanes-ethyl acetate) indicated that a new nonpolar spot (R$_f$=0.50) had formed with some starting material remaining. The temperature was then increased to 55-60° C. and the reaction stirred for 14 hours. TLC showed a new polar spot (R$_f$=0.25) with no furan remaining. The solvent was then removed under reduced pressure. Column purification (4:6 to 1.5:8.5, hexanes-ethyl acetate) was carried out to obtain 191 mg of the endo product (25% yield) and 26 mg (4% yield) of the exo product. Due to the fact that these compounds have an inherently unstable nature at ambient temperatures, they are kept stored at −20° C. until required.

rac-(3aR,4R,7R,7aS)-4-(hydroxymethyl)-7-methoxy-2-(4-methoxyphenyl)-3a,4,7,7a-tetrahydro-1H-4,7-epoxyisoindole-1,3(2H)-dione (45$_{endo}$)

White solid; R$_f$=0.50 (2:8, hexanes-ethyl acetate); $^1$H NMR (300 MHz, CD$_3$CN): δ$_{ppm}$ 7.03 (d, J=9.10 Hz, 2H), 6.98 (d, J=9.14 Hz, 2H), 6.63 (d, J=5.82 Hz, 1H), 6.58 (d, J=5.83 Hz, 1H), 4.10 (dd, J=12.91, 5.81 Hz, 1H), 3.99 (dd, J=12.91, 6.13 Hz, 1H), 3.81 (s, 3H), 3.71 (d, J=7.87 Hz, 1H), 3.56 (s, 3H), 3.51 (d, J=7.90 Hz, 1H), 3.20 (t, J=6.02, Hz, 1H, OH); $^{13}$C NMR (125 MHz, CDCl3): δ$_{ppm}$ 174.5, 173.8, 159.8, 137.7, 134.9, 128.2, 128.2, 124.9, 114.4, 86.8, 60.7, 55.3, 54.1, 50.2, 48.9. HRMS (CI): Calculated for [M]+ (C$_{17}$H$_{17}$NO$_6$): 331.1056, [M+H]+: 332.1134. Found [M+H]+: 332.1127.

rac-(3aR,4R,7R,7aS)-4-(hydroxymethyl)-7-methoxy-2-(4-methoxy phenyl)-3a,4,7,7a-tetrahydro-1H-4,7-epoxyisoindole-1,3(2H)-dione (45$_{exo}$)

White solid; R$_f$=0.25 (2:8, hexanes-ethyl acetate); $^1$H NMR (300 MHz, CDCl$_3$): δ$_{ppm}$ 7.21 (d, J=8.94 Hz, 2H), 6.97 (d, J=9.01 Hz, 2H), 6.79 (d, J=5.66 Hz, 1H), 6.56 (d, J=5.66 Hz, 1H), 4.14 (d, J=12.65 Hz, 1H), 4.08 (d, J=12.71 Hz, 1H), 3.82 (s, 3H), 3.63 (s, 3H), 3.27 (d, J=6.59 Hz, 1H), 3.21 (d, J:=6.57 Hz, 1H).

rac-(3aR,4R,7R,7aS)-4-(hydroxymethyl)-7-methoxy-2-(4-nitrophenyl)-3a,4,7,7a-tetrahydro-1H-4,7-epoxyisoindole-1,3(2H)-dione (46$_{endo}$) and rac-(3aS,4R,7R,7aR)-4-(hydroxymethyl)-7-methoxy-2-(4-nitrophenyl)-3a,4,7,7a-tetrahydro-1H-4,7-epoxyisoindole-1,3(2H)-dione (46$_{exo}$)

N-(p-nitrophenyl)-Maleimide 6 (458 mg, 2.1 mmol) and 5-methoxy-2-furanmethanol 4 (320 mg g, 2.5 mmol) were dissolved in anhydrous acetonitrile under a nitrogen atmosphere in a flame-dried flask equipped with a magnetic stirring-bar. The reaction was stirred at 45° C. for 4 hours and then 80° C. for an additional 8; TLC analysis (2:8, hexanes-ethyl acetate) indicated that a new nonpolar spot (R$_f$=0.50) and polar spot had formed (R$_f$=0.21). The solvent was then removed under reduced pressure. Column purification (4:6 to 1.5:8.5, hexanes-ethyl acetate) was carried out to obtain 400 mg of the endo product (52% yield) and approximately 30 mg of the exo product (4% yield). Due to the fact that these compounds have an inherently unstable nature at ambient temperatures, they are kept stored at −20° C. until required.

rac-(3aR,4R,7R,7aS)-4-(hydroxymethyl)-7-methoxy-2-(4-nitrophenyl)-3a,4,7,7a-tetrahydro-1H-4,7-epoxyisoindole-1,3(2H)-dione (46$_{endo}$)

White solid; R$_f$=0.50 (2:8, hexanes-ethyl acetate); $^1$H NMR (300 MHz, CD$_3$CN): δ$_{ppm}$ 8.30 (d, J=9.08 Hz, 2H), 7.43 (d, J=9.08 Hz, 2H), 6.65 (d, J=5.87 Hz, 1H), 6.60 (d, J=5.81 Hz, 1H), 4.12 (dd, J=12.95, 5.84 Hz, 1H), 4.01 (dd, J=12.90, 6.21 Hz, 1H), 3.80 (d, J=7.89 Hz, 1H), 3.59 (d, J=7.91 Hz, 1H), 3.57 (s, 3H), 3.24 (t, J=6.02 Hz, 1H, OH); $^{13}$C NMR (125 MHz, CDCl$_3$): δ$_{ppm}$ 173.5, 172.8, 147.5, 137.8, 137.6, 135.0, 127.7, 124.4, 114.5, 86.9, 60.6, 54.2, 50.5, 49.1; HRMS (CI): Calculated for [M]+ (C$_{16}$H$_{14}$N$_2$O$_7$): 346.0801. [M+H]+ (C$_{16}$H$_{15}$N$_2$O$_7$): 347.0879. Found: 347.0874.

rac-(3aS,4R,7R,7aR)-4-(hydroxymethyl)-7-methoxy-2-(4-nitrophenyl)-3a,4,7,7a-tetrahydro-1H-4,7-epoxyisoindole-1,3(2H)-dione (46$_{exo}$)

R$_f$=0.21 (2:8, hexanes-ethyl acetate); $^1$H NMR (300 MHz, CD$_3$CN): δ$_{ppm}$ 8.48 (d, J=8.93 Hz, 2H), 7.69 (d, J=8.92 Hz, 2H), 6.89 (d, J=5.68 Hz, 1H), 6.79 (d, J=5.49 Hz, 1H), 4.29 (d, J=12.03 Hz, 1H), 4.11 (d, J=12.77 Hz, 1H), 3.72 (s, 3H), 3.50-3.27 (m, 2H).

2-benzyl-4-(hydroxymethyl)-7-methoxyisoindoline-1,3-dione (47)

N-benzyl maleimide 7 (490 mg, 2.6 mmol) and 5-methoxy-2-furanmethanol 4 (400 mg g, 3.0 mmol) were dissolved in anhydrous acetonitrile under a nitrogen atmosphere in a flame-dried flask equipped with a magnetic stirring-bar. The reaction was stirred at 40° C. for 4 hours, and 50° C. for 18 hours after which no reaction was observed. The reaction mixture was then further heated to 65° C. for an additional 4 hours at which point a new spot was observed by TLC (Rf=0.35, 2:8, hexanes-ethyl acetate). The solvent was then removed under reduced pressure. Column purification (4:6 to 1.5:8.5, hexanes-ethyl acetate) was carried out to obtain 530 mg of a single product, the title compound, in 60% yield as a white solid.

White solid. R$_f$=0.35 (2:8, hexanes-ethyl acetate); $^1$H NMR (300 MHz, CDCl$_3$): δ$_{ppm}$ 7.47 (d, J=8.58 Hz, 1H), 7.39-7.31 (m, 2H), 7.28-7.13 (m, 3H), 7.05 (d, J=8.59 Hz, 1H), 4.78 (s, 2H), 4.74 (s, 2H), 3.93 (s, 3H); $^{13}$C NMR (125 MHz, CDCl$_3$): δ$_{ppm}$ 169.3, 166.5, 156.2, 136.2, 135.9, 132.9, 130.9, 128.73, 128.65, 127.8, 117.6, 117.5, 61.9, 56.4, 41.5. HRMS (CI): Calculated for [M]+ (C$_{17}$H$_{16}$NO$_4$): 297.1001, [M+H]+ (C$_{17}$H$_{16}$NO$_4$): 298.1079. Found: 298.1075.

Synthesis of Protecting Groups:
Synthesis of Benzyl-H Protecting Group JT70B

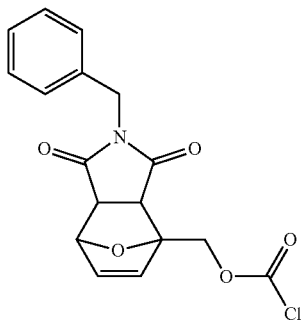 [SMILES: O=C(Cl)OCC12C=CC(O1)C1C(=O)N(Cc3ccccc3)C(=O)C12]

(2-benzyl-1,3-dioxo-2,3,3a,4,7,7a-hexahydro-1H-4,7-epoxyisoindol-4-yl)methyl-carbonochloridate (103)

2-Benzyl-4-(hydroxymethyl)-3a,4,7,7a-tetra-hydro-1H-4,7-epoxyisoindole-1,3(2H)-dione (102) (0.25 g, 0.876 mmol) was dissolved in dry toluene (5.0 ml) under nitrogen. Once cooled to 0° C., N,N-diisopropylethylamine (0.46 ml) was added to the solution. Triphosgene (139.9 mg) was subsequently added to the solution. The reaction was stirred under nitrogen for 2 hours at 0° C., and was then stirred for 12 hours at 25° C. The reaction mixture was extracted once with ethyl acetate (10 ml). The organic fraction was washed once with a solution of ammonium chloride (15 ml), and once more with a solution of acidic brine (15 ml). The organic phase was subsequently dried with anhydrous MgSO$_4$ and concentrated under reduced pressure to deliver the title compound (0.221 g, 75% yield). Rf 0.71 in 3:7 hexane/ethyl acetate. $^1$H NMR (300 MHz, CDCl$_3$) δ 7.42-7.24 (m, 10H), 7.24-7.15 (m, 2H), 6.23 (dd, J=5.8, 1.7 Hz, 1H), 6.04 (d, J=5.8 Hz, 1H), 5.42-5.26 (m, 1H), 5.13-4.97 (m, 1H), 4.91-4.63 (m, 2H), 4.52 (s, 2H), 3.70 (dd, J=7.7, 5.5 Hz, 1H), 3.41 (d, J=7.7 Hz, 1H). $^{13}$C NMR (300 MHz, CDCl$_3$) δ$_{ppm}$ 137.6, 137.2, 135.4, 135.1, 134.6, 129.1, 128.5, 125.3, 90.4, 81.1, 79.6, 68.3, 62.7, 61.9, 50.2, 48.5, 47.9, 46.8, 42.4, 29.8, 22.8, 21.7, 20.7, 16.0.

MS Calculated for C$_{17}$H$_{14}$ClNO$_5$ [M+H]+: 348.7500. Found (ASAP): 348.0639.

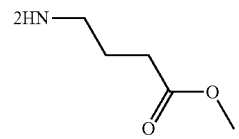

Methyl 4-aminobutanoate (104)

4-aminobutanoic acid (5.0 g, 48.5 mmol) was dissolved in methanol (75.0 ml) and allowed to stir at 0° C. for 15 minutes. Thionyl chloride (5.27 ml) was slowly added dropwise and the reaction was stirred at 0° C. for 1.5 hours. The solvent was evaporated at reduced pressure and the titled compound was delivered (4.97 g, 87%). $^1$H NMR (300 MHz, CDCl$_3$) δ$_{ppm}$ 3.37 (s, 3H), 3.03 (t, J=7.3 Hz, 2H), 2.53 (t, J=7.9 Hz, 2H), 1.99 (p, J=7.5 Hz, 2H).

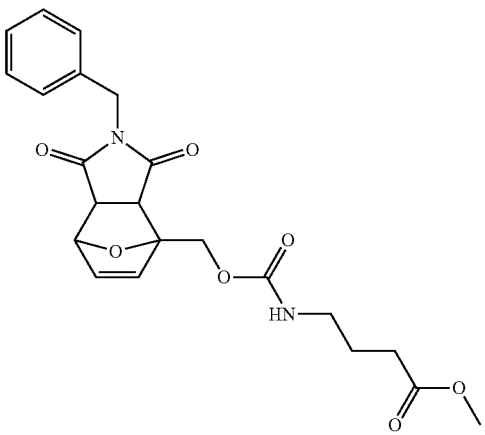 [SMILES: COC(=O)CCCNC(=O)OCC12C=CC(O1)C1C(=O)N(Cc3ccccc3)C(=O)C12]

methyl 4-((((2-benzyl-1,3-dioxo-2,3,3a,4,7,7a-hexahydro-1H-4,7-epoxyisoindol-4-yl)methoxy)carbonyl)amino)butanoate (105)

(2-benzyl-1,3-dioxo-2,3,3a,4,7,7a-hexahydro-1H-4,7-epoxyisoindol-4-yl)methyl-carbonchloridate (103) (500 mg, 1.63 mmol) was dissolved in chloroform (2.0 ml) under nitrogen, and cooled to 0° C. N,N-diisopropylethylamine (0.851 ml) was then added to the solution, followed by the addition of ethyl 4-aminobutanoate (104) (228.8 mg, 1.956 mmol). The mixture was stirred under nitrogen at room temperature for 6 hours. The reaction mixture was diluted with 10% hydrochloric acid (2 ml), and the resulting solution was extracted once with chloroform (2 ml). The organic fraction was washed once more with saturated sodium bicarbonate (2 ml) and once more with brine (2 ml). The resulting organic fraction was dried with anhydrous MgSO$_4$ and concentrated under reduced pressure in order to yield the titled compound as a waxy solid (302.1 mg, 43%) Rf 0.24 in 1:1 hexane/ethyl acetate. $^1$H NMR (300 MHz, DMSO) δ 7.39-7.12 (m, 5H), 6.59 (d, J=5.7 Hz, 1H), 6.45 (d, J=5.7 Hz, 1H), 5.16 (d, J=1.8 Hz, 1H), 4.77 (d, J=12.8 Hz, 1H), 4.57 (s, 2H), 4.15 (d, J=12.7 Hz, 1H), 3.57 (s, 2H), 3.16 (d, J=6.4 Hz, 1H), 3.07 (s, 1H), 3.05-2.92 (m, 2H), 2.30 (t, J=7.4 Hz, 2H). $^{13}$C NMR (75 MHz, DMSO) δ 174.53, 173.05, 155.75, 135.77, 135.50, 134.54, 128.32, 127.81, 127.42, 89.78, 79.17, 78.78, 61.57, 51.23, 47.43, 46.17, 41.40, 30.51, 28.35, 24.65, 10.79.

MS Calculated for C$_{22}$H$_{24}$N$_2$O$_7$ [M+H]$^+$: 429.44. Found (ASAP): 429.1678.

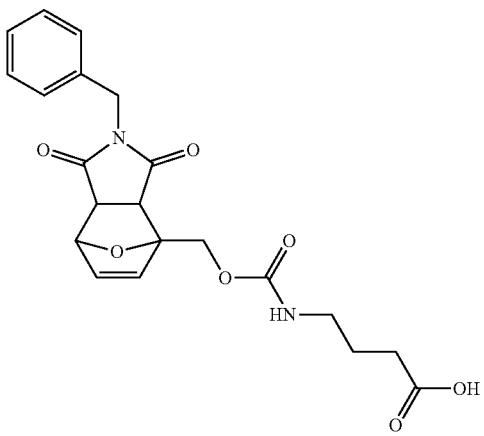 [SMILES: O=C(O)CCCNC(=O)OCC12C=CC(O1)C1C(=O)N(Cc3ccccc3)C(=O)C12]

4-((((2-benzyl-1,3-dioxo-2,3,3a,4,7,7a-hexahydro-1H-4,7-epoxyisoindol-4-yl)methoxy)carbonyl)amino)butanoic acid (106)

Methyl 4-((((2-benzyl-1,3-dioxo-2,3,3a,4,7,7a-hexahydro-1H-4,7-epoxyisoindol-4-yl)methoxy)carbonyl)amino)butanoate (105) (200 mg, 0.467 mmol) was dissolved in 1,4-dioxane (0.92 ml) and 2N NaOH (4.00 ml). The resulting solution was stirred at 45'C for 24 hours, and subsequently cooled to room temperature. The reaction mixture was diluted with ethyl acetate (5 ml) and then acidified to pH 1 with the dropwise addition of 2N hydrochloric acid. Dichloromethane (5 ml) was added to the solution, and the organic and aqueous phases were separated. The aqueous fraction was stored at 0'C for 12 hours, and the titled compound was obtained (100 mg, 53% yield) appearing as white crystals which formed in the aqueous layer. $^1$H NMR (300 MHz, DMSO) δ$_{ppm}$ 12.07 (s, 1H), 8.38 (s, 1H), 7.28 (m, 5H), 6.47 (d, J=4.9 Hz, 1H), 6.26 (d, J=6.0 Hz, 1H), 5.09 (s, 1H), 4.58 (d, J=12.3 Hz, 1H), 4.32 (m, 1H), 4.20 (m, 1H), 4.04 (d, 12.0 Hz, 1H), 2.98 (m, 2H), 2.81 (d, J=8.7 Hz, 1H), 2.64 (d, J=8.7 Hz, 2H), 1.60 (m, 2H).

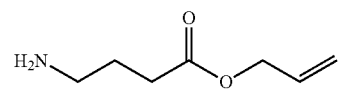

Allyl 4-aminobutanoate (149)

At 0° C. and under nitrogen atmosphere, acetyl chloride (4.6 mL, 56.2 mmol) was added dropwise into a flame dried flask of allyl alcohol (20 mL). It was stirred it for at least 30 minutes then add 4-GABA (2.0 g, 19.4 mmol) slowly. It was refluxed overnight then cooled and evaporated in the morning under a ventilated fume hood. The concentrated mixture was diluted with ethyl acetate then quenched with saturated sodium bicarbonate. The organic layer was separated, and another extraction by ethyl acetate was performed. The organic layer was then washed with brine then dried with magnesium sulfate. A silica column was used to purify the crude at 4:6 methanol/ethyl acetate with the product being the first to elute. The titled compound ranged from light to dark brown oil (47%). Rf 0.7 in 4:6 hexane/ethyl acetate under vanillin stain. $^1$H NMR (300 MHz, CDCl$_3$) δ 5.93-5.74 (m, 1H), 5.34-5.13 (m, 2H), 4.51 (dt, J=5.8, 1.4 Hz, 2H), 3.09 (t, J=7.6 Hz, 2H), 2.49 (t, J=7.2 Hz, 2H), 2.07 (p, J=7.3 Hz, 2H).

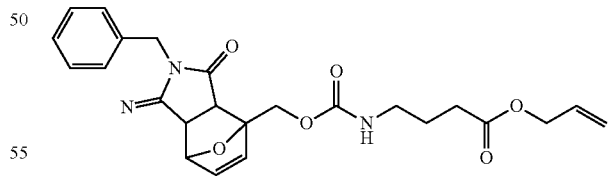

Allyl 4-((((2-benzyl-1,3-dioxo-2,3,3a,4,7,7a-hexahydro-1H-4,7-epoxyisoindol-4-yl)methoxy)carbonyl)amino)butanoat (150)

The endcap (103) (722 mg, 2.08 mmol) was dissolved in 3 mL of chloroform and cooled to 0° C. DIPEA (1.7 ml) was subsequently added to the solution and followed by addition of the allyl 4-aminobutanoate (357 mg, 2.49 mmol). The mixture was stirred under nitrogen in room temperature until starting material is consumed. The reaction mixture was washed the with 10% HCl (3 ml) and was extracted with chloroform (3 ml) twice. The organic fraction was subsequently washed with saturated sodium bicarbonate (4 ml) and once more with brine (4 ml). The resulting organic fraction was dried with anhydrous MgSO$_4$ and concentrated under reduced pressure and the crude mixture was purified by silica column chromatography in order to yield the title compound as a brown oil (39%) R$_f$ 0.47 endo/0.29 exo in 1:1 hexane/ethyl acetate.

$^1$H NMR (300 MHz, CDCl3) δ 7.31-7.20 (m, 6H), 6.12 (dd, J=5.8, 1.6 Hz, 1H), 6.02 (d, J=5.8 Hz, 1H), 5.88 (ddt, J=17.2, 10.4, 5.8 Hz, 1H), 5.22 (ddt, J=11.7, 7.9, 1.4 Hz, 3H), 5.02 (s, 1H), 4.59-4.51 (m, 3H), 4.44 (s, 2H), 3.59 (dd, J=7.7, 5.5 Hz, 1H), 3.21 (q, J=6.6 Hz, 2H), 2.36 (d, J=14.6 Hz, 2H), 1.82 (t, J=7.1 Hz, 2H). $^{13}$C NMR (76 MHz, CDCl$_3$) δ 174.07, 173.86, 172.64, 155.63, 135.25, 135.17, 134.27, 131.97, 128.91, 128.36, 127.91, 118.25, 89.97, 79.50, 65.09, 62.32, 47.52, 46.45, 42.21, 40.34, 31.21, 30.78, 24.89. MS Calculated for C$_{24}$H$_{26}$N$_2$O$_7$: 455.1818. Found (ASAP): 455.1817.

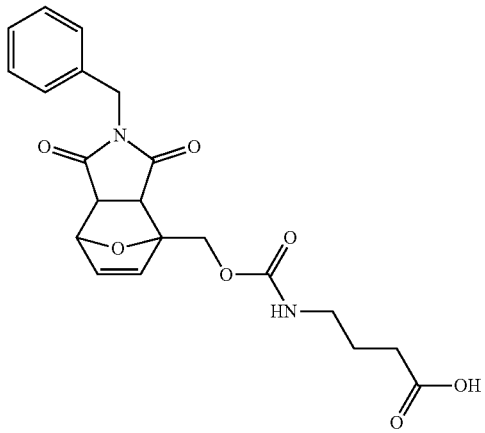 [SMILES: O=C(O)CCCNC(=O)OCC12C=CC(O1)C1C(=O)N(Cc3ccccc3)C(=O)C12]

4-((((2-benzyl-1,3-dioxo-2,3,3a,4,7,7a-hexahydro-1H-4,7-epoxyisoindol-4-yl)methoxy)carbonyl)amino)butanoic acid (151)

(Allyl 4-((((2-benzyl-1,3-dioxo-2,3,3a,4,7,7a-hexahydro-1H-4,7-epoxyisoindol-4-yl)methoxy)carbonyl)amino)butanoate (150) (50 mg, 0.11 mmol) was dissolved in THF (1.5 ml) in a flame dried round bottom flask under nitrogen atmosphere. Then morpholine (0.09 ml, 1.1 mmol) and tetrakis(triphenylphosphine)-palladium (11.6 mg, 0.01 mmol) were subsequently added. The reaction was left stirring at room temperature until starting material was consumed. The mixture was filtered and evaporated then washed with 10% HCl (1 ml) and extracted with DCM. A column starting at 3:7 to 1:1 hexane/ethyl acetate to flush out the nonpolar components, then increased polarity to bring the titled compound down with at least 7:3 hexane/ethyl acetate. The titled compound was obtained (32% yield) appearing as yellow oil. Rf 0.19 in 1:1 hexane/ethyl acetate.

$^1$H NMR (300 MHz, DMSO) δ$_{ppm}$ 12.07 (s, 1H), 8.38 (s, 1H), 7.28 (m, 51H), 6.47 (d, J=4.9 Hz, 1H), 6.26 (d, J=6.0 Hz, 1H), 5.09 (s, 1H), 4.58 (d, J=12.3 Hz, 1H), 4.32 (m, 1H), 4.20 (m, 1H), 4.04 (d, 12.0 Hz, 1H), 2.98 (m, 2H), 2.81 (d, J=8.7 Hz, 1H), 2.64 (d, J=8.7 Hz, 2H), 1.60 (m, 2H).

Synthesis of Protected Cysteines:

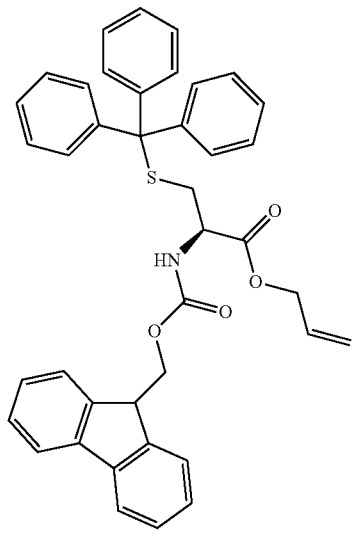 [SMILES: C=CCOC(=O)[C@H](CSC(c1ccccc1)(c1ccccc1)c1ccccc1)NC(=O)OCC1c2ccccc2-c2ccccc21]

Allyl 2-((((9H-fluoren-9-yl)methoxy)carbonyl) amino)-3-(tritylthio)propanoate (200)

Fmoc-Cys(Trt)-OH (100 mg, 0.17 mmol) was dissolved in ethanol (1.25 ml) and an equimolar amount of cesium carbonate (55.4 mg, 0.17 mmol) was subsequently added to the solution. The ethanol solvent was distilled off at reduced pressure, and the remaining residue was taken up multiple times by benzene and evaporated to dryness. The formed cesium salt was dissolved in dimethylformamide (0.25 ml) and allyl bromide (0.34 ml, 4 mmol) was subsequently added to the solution (225.2 mg, 1.86 mmol). The resulting mixture was stirred at room temperature for 18 hours. The solvent was then evaporated under reduced pressure, and the crude mixture was purified by silica column chromatography in order to yield the title compound (76.6 mg, 72% yield) R$_f$ 0.44 in 1:4 hexane/ethyl acetate.

$^1$H NMR (300 MHz, DMSO) δ 7.90 (p, J=10.0, 9.1 Hz, 3H), 7.72 (d, J=7.5 Hz, 2H), 7.49-7.13 (m, 23H), 5.91-5.61 (m, 1H), 5.25-5.05 (m, 2H), 4.47 (d, J=5.2 Hz, 2H), 4.36-4.09 (m, 3H), 3.86 (td, J=9.2, 4.8 Hz, 1H), 2.67 (dd, J=12.8, 10.0 Hz, 1H). $^{13}$C NMR (75 MHz, DMSO) δ 170.29, 156.07, 144.42, 144.03, 143.96, 141.00, 132.34, 129.37, 128.40, 127.92, 127.34, 127.15, 125.51, 120.40, 117.71, 66.76, 66.04, 65.24, 53.79, 46.85, 32.96. (Gaussian 3.40 Hz apodization)

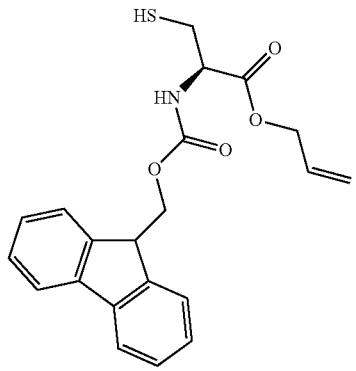 [SMILES: C=CCOC(=O)[C@H](CS)NC(=O)OCC1c2ccccc2-c2ccccc21]

Allyl-2-((((9H-fluoren-9-yl)methoxy)carbonyl)amino)-3-mercaptopropanoate (201)

Allyl 2-((((9H-fluoren-9-yl)methoxy)carbonyl)amino)-3-(tritylthio)propanoate (200) (100 mg, 0.16 mmol) was dissolved in DCM (2.0 ml) and stirred at 0° C. for 15 minutes. Triethylsilane (23.0 mg, 0.19 mmol) was added to the mixture, followed by the addition of TFA (0.2 ml). The mixture was stirred at room temperature for 1 hour. The solvent was removed via nitrogen blowdown evaporation and the resultant crude mixture was purified by silica column chromatography in order to yield the title compound (37.1 mg, 61% yield)

$^1$H NMR (300 MHz, CDCl3) δ 7.86-7.67 (m, 21H), 7.59 (s, 2H), 7.50-7.23 (m, 4H), 5.99-5.66 (m, 1H), 5.42-5.17 (m, 1H), 4.68 (d, J=7.1 Hz, 2H), 4.39 (d, J=7.2 Hz, 2H), 4.30-4.18 (m, 1H), 3.09 (dq, J=28.8, 17.2, 9.8 Hz, 2H). $^{13}$C NMR (76 MHz, CDCl3) δ 170.89, 170.59, 156.42, 156.30, 144.75, 144.28, 144.19, 144.05, 141.80, 134.49, 132.93, 131.81, 130.01, 129.93, 128.78, 128.54, 128.25, 127.60, 127.42, 127.28, 126.79, 126.63, 125.63, 125.34, 124.39, 120.50, 119.78, 119.66, 119.61, 119.28, 118.53, 117.71, 67.88, 67.10, 67.00, 66.96, 66.63, 56.93, 55.73, 53.96, 53.31, 47.65, 47.58, 47.54, 41.59, 35.17, 34.53, 33.15, 32.08, 31.21, 28.12, 27.42, 25.79, 23.15, 14.62. (Gaussian 3.7 Hz appodization).

Coupling of Endcap Containing Various Linkers with Cysteines:

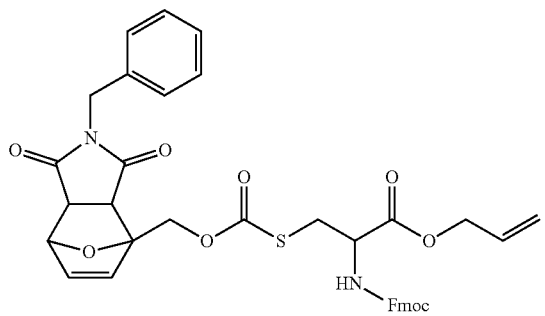

Fmoc-Cys-(S-Benzyl-maleimide)-(O-allyl) ((188)

Allyl-2-((((9H-fluoren-9-yl)methoxy)carbonyl)amino)-3-mercaptopropanoate (94.3 mg) was dissolved in THF (2 ml) and cooled in ice bath to 0° C. 3 equimolar amount of DIPEA (0.06 ml) was subsequently added to the solution, followed by the addition of endcap (103) (1 eq, 50 mg). The mixture was stirred under nitrogen at room temperature. The reaction mixture was diluted with 10% hydrochloric acid (10 ml), and the resulting solution was extracted with ethyl acetate (30 ml) two times. The organic fraction was washed once more with saturated sodium bicarbonate (10 ml) and once more with brine (20 ml). The resulting organic fraction was dried with anhydrous MgSO$_4$ and concentrated under reduced pressure and the crude mixture was purified by silica column chromatography in order to yield the title compound as solid (76.6 mg, 72% yield) R$_f$0.38 in 1:1 hexane/ethyl acetate. $^1$H NMR (300 MHz, CDCl$_3$) δ 7.42-7.24 (m, 10H), 7.24-7.15 (m, 2H), 6.23 (dd, J=5.8, 1.7 Hz, 1H), 6.04 (d, J=5.8 Hz, 1H), 5.42-5.26 (m, 1H), 5.13-4.97 (m, 1H), 4.91-4.63 (m, 2H), 4.52 (s, 2H), 3.70 (dd, J=7.7, 5.5 Hz, 1H), 3.41 (d, J=7.7 Hz, 1H). $^{13}$C NMR (76 MHz, CDCl3) δ 174.35, 170.93, 156.32, 144.32, 141.87, 136.65, 135.77, 134.78, 133.80, 131.91, 129.67, 129.47, 129.27, 129.12, 128.97, 128.75, 128.29, 127.65, 126.59, 125.71, 120.55, 119.73, 118.53, 89.51, 80.47, 68.75, 67.87, 67.04, 66.60, 60.96, 56.99, 54.00, 48.06, 47.65, 46.94, 43.04, 33.29.31.31, 14.77.

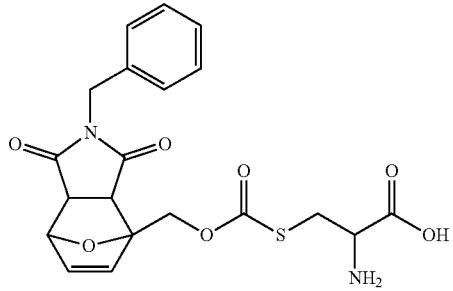

Fmoc-Cys-(S-Benzyl-maleimide)-OH (216)

Fmoc-Cys-(S-Benzyl-maleimide)-(O-allyl) (188) (50 mg, 0.072 mmol) was dissolved in THF (10 mL, 1 mmol) and morpholine (0.062 mL, 0.72 mmol). The resulting solution was stirred under nitrogen at room temperature overnight, and subsequently added Pd(PPh$_3$)$_4$ (4.15 mg, 0.0036 mmol). After consumption of the starting material, the reaction mixture was diluted with 10% hydrochloric acid (5 ml), and the resulting solution was extracted with ethyl acetate (15 ml) two times and was washed once more with brine (10 ml). The resulting organic fraction was dried with anhydrous MgSO$_4$ and concentrated under reduced pressure and the crude mixture was purified by silica column chromatography in order to yield the title compound as solid (20 mg, 40% yield) Rf 0.2 in 1:1 hexane/ethyl acetate.

$^1$H NMR (300 MHz, CDCl$_3$) δ 7.75-7.60 (m, 2H), 7.60-7.38 (m, 4H), 7.38-7.22 (m, 13H), 6.62 (d, J=5.7 Hz, 1H), 6.54 (dd, J=5.7, 1.7 Hz, 1H), 6.16 (dd, J=5.8, 1.6 Hz, 1H), 6.07 (d, J=5.8 Hz, 1H), 5.34-5.20 (m, 2H), 4.67 (s, 2H), 4.48 (s, 2H), 4.34-3.98 (m, 4H), 3.64 (dd, J=7.7, 5.5 Hz, 1H), 3.41 (d, J=7.6 Hz, 1H), 3.05-2.93 (m, 2H). $^{13}$C NMR (76 MHz, CDCl3) δ 175.83, 175.64, 174.89, 174.42, 138.44, 137.01, 135.40, 135.26, 134.60, 132.19, 132.06, 131.99, 131.95, 129.08, 128.71, 128.61, 128.52, 128.45, 128.14, 128.09, 127.94, 92.07, 91.46, 80.95, 79.63, 61.62, 60.85, 50.02, 48.22, 48.04, 46.18, 42.63, 42.40, 29.72. (Gussain 1.60)

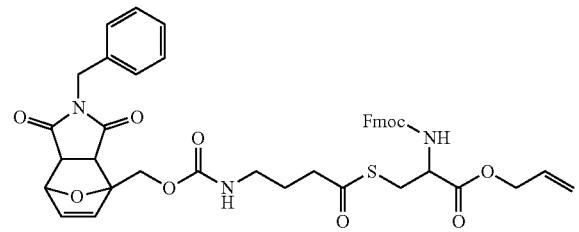

Fmoc-Cys-(S-4-aminobutyric-N-Benzyl-maleimide)-(O-allyl) (222)

Endcap (151) (67.7 mg, 0.216 ml) was dissolved in DMF (0.5 ml) and cooled to 0° C. 3 equimolar amount of DIPEA (0.06 ml) was subsequently added to the solution, followed by the addition of EDC (38.53 mg, 0.273 mmol) and HOBT (30.71 mg, 1.1 eq). The mixture was stirred under nitrogen for 10 minutes. Then Allyl-2-((((9H-fluoren-9-yl)methoxy)carbonyl)amino)-3-mercaptopropanoate (201) (105.16 mg, 0.324 mmol) was added to the mixture and stirred under nitrogen overnight. The reaction mixture was diluted with ethyl acetate (20 ml) two times and then acidified with the 10% hydrochloric acid. The organic fraction was washed once more with saturated sodium bicarbonate (8 ml) and once more with brine (15 ml). The resulting organic fraction was dried with anhydrous $MgSO_4$ and concentrated under reduced pressure and the crude mixture was purified by silica column chromatography in order to yield the title compound as solid (11 mg, 16.2% yield) Rf 0.13 in 1:1 hexane/ethyl acetate.

$^1$H NMR (300 MHz, $CDCl_3$) δ 7.76 (t, J=7.0 Hz, 3H), 7.69-7.50 (m, 3H), 7.50-7.22 (m, 8H), 6.03-5.82 (m, 4H), 5.76 (d, J=8.2 Hz, 1H), 5.66 (d, J=8.3 Hz, 1H), 5.48-5.04 (m, 9H), 4.63 (dt, J=22.9, 5.9 Hz, 12H), 4.41 (dq, J=12.8, 8.6, 6.4 Hz, 3H), 4.23 (dt, J=13.4, 7.1 Hz, 2H), 3.79 (d, J=4.4 Hz, 1H), 3.22-2.84 (m, 6H), 1.42 (p, J=5.7 Hz, 1H), 1.34-1.16 (m, 2H).

Evaluation of Thermal Sensitivity of End-Caps:
Details Regarding the Kinetic Studies In other experiments, kinetic studies were carried out in an NMR tube (see FIGS. 3 and 4). All samples were prepared in the same way. Forward Diels-Alder reactions: 5.65 mg of furan (5.0 µL, 0.057 mmol) and an equimolar amount of the maleimide was added directly to 750 µL of deuterated solvent (either acetonitrile-d3 or more often DMSO-d6 for any reaction 70° C. or above). For reverse Diels-Alder reactions, 16.0 mg of cycloadduct was added to 3.0 mL of deuterated solvent in a vial. The solution was then partitioned between 4 NMR tubes and stored at −20° C. until used for an experiment. The experiments were carried out at the indicated temperatures on a Bruker 300 $^1$H NMR spectrometer equipped with a variable temperature probe. A blank NMR tube containing the solvent but no analyte was inserted into the probe and the spectrometer was allowed to equilibrate to the indicated temperature for 10 minutes. The tube was then switched for the sample, and the experiment was run with a spectrum being collected every minute for the first 11 minutes, and then every 5 minutes thereafter for a total of four hours using the multi_zgvd script in the Bruker Topspin suite (8 scans per spectrum). Following data collection, the first and last spectra of the series were examined. If there was no change (and no appearance of starting material or product as determined by comparison of the spectra with those of previously isolated samples), no further action was taken, and conversion was determined to effectively be 0%. If any integration was noted in the final spectrum at the frequency corresponding to the peaks of the relevant reaction products, then all spectra in the series were integrated over identical frequency ranges. The data was exported to .txt files, imported into excel and converted to reaction conversions. Initial rates were calculated based on the first four data points. In all observed cases, this region was effectively linear. The time required to obtain 25% conversion was determined by a simple linear interpolation between the relevant data points. This value is arbitrary, but a half-life was considered to be a non accurate measurement as many of the cycloreversions plateau before 50% conversion due to the equilibrium kinetics of the system. The 25% conversion point was generally observed in the early stages of the cycloreversion and was selected as a meaningful surrogate for our own use of these systems, and will potentially play the same role for other researchers.

Synthesis of Linear Peptides:

The syntheses of the peptides were carried out using an AAPTTEC FocusXC-6RV automated peptide synthesizer (6 reaction vessels), equipped with an argon atmosphere, mechanical and gas-bubbling shaking systems, and a reaction vessel heating and/or cooling system controlled from an IBM PC using Focus XC software (v. 3.03). Preloaded Fmoc-Gly-Wang or Fmoc-Ala-Wang resins were swollen in DMF for 1 hour followed by filtration, and then were subjected to 20% piperidine in DMF twice successively for 30 mins. Peptide couplings were carried out according to standard protocols for Fmoc solid phase synthesis using HCTU as coupling agent (see Chan, W. C. et al., Basic procedures. In *Fmoc Solid Phase Peptide Synthesis: A Practical Approach*, Chan, W. C.; White. P. D., Eds. Oxford University Press: Oxford, 2000; pp 41-76, the entire contents of which are incorporated herein by reference). All residues were coupled using 5 equivalents of amino acid per functionalized position on the resin with 1 hour reaction times. All couplings were carried out as double couplings. Following the coupling of each residue deprotection of the Fmoc moiety was accomplished by treatment with 20% piperidine in DMF twice successively for 30 mins. Before and after each coupling, the beads were shaken 4 times with 4 mL of DMF followed by filtration. Following the synthesis the beads were washed extensively with DMF (6×4 mL), MeOH (6×4 mL), DCM (6×4 mL), hexanes (6×4 mL), and finally by ethanol (3×6 mL) and then removed from the synthesizer and stored in a desiccator under vacuum in the presence of $P_2O_5$ until required. A small amount cleaved from the resin using 92.5:5:2.5 (v/v/v) TFA:triisopropylsilane:water. The peptide was purified using RP-HPLC (ramp from 0% to 18% acetonitrile in water over 5 mins followed by isocratic flow for 25 mins) unless otherwise stated.

While the invention has been described with reference to preferred embodiments, the invention is not or intended by the applicant to be so limited. A person skilled in the art would readily recognize and incorporate various modifications, additional elements and/or different combinations of the described components consistent with the scope of the invention as described herein.

We claim:

1. A protected cysteine having structural formula 9 or 10:

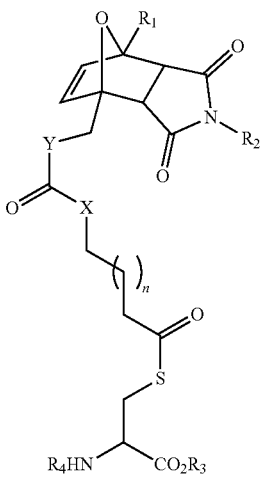

9

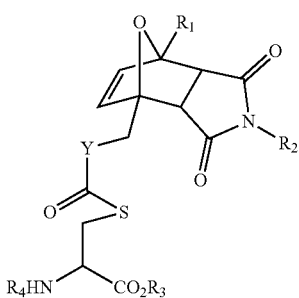

wherein

X and Y are independently of each other oxygen, sulfur, nitrogen or phosphorus;

$R_1$ and $R_2$ are independently of each other hydrogen, hydroxyl, halo, alkyl, alkenyl, alkynyl, cycloalkyl, heterocycloalkyl, aryl, aralkyl, heteroaryl, heteroaralkyl, formyl, haloformyl, carbonyl, carboxyl, alkoxy, alkoxycarbonyl, (alkoxycarbonyl)oxy, carbamoyl, amino, amido, imino, imido, azo, cyanato, isocyanato, cyano, nitro, sulfanyl, thiocyanato or phosphono, each of which is optionally substituted;

$R_3$ and $R_4$ are independently each other hydrogen or a protecting group; and n is an integer between 1 and 12, inclusive.

2. The protected cysteine of claim 1, wherein $R_1$ and $R_2$ are independently of each other hydrogen, hydroxyl, halo, alkyl, cycloalkyl, heterocycloalkyl, aryl, heteroaryl, formyl, carbonyl, carboxyl, alkoxy, amino or nitro, each of which is optionally substituted.

3. The protected cysteine of claim 1, wherein $R_1$ is hydrogen, hydroxyl, halo, alkyl, formyl, carbonyl, carboxyl, alkoxy, alkoxycarbonyl, amino or nitro, each of which is optionally substituted, and $R_2$ is hydrogen, alkyl, cycloalkyl, heterocycloalkyl, aryl or heteroaryl, each of which is optionally substituted.

4. The protected cysteine of claim 1, wherein $R_1$ is hydrogen, nitro, halo or alkoxy, and $R_2$ is alkyl, aryl or heteroaryl, each of which is optionally substituted or wherein $R_1$ is hydrogen, nitro, bromo, chloro, fluoro, methoxy or ethoxy, and $R_2$ is methyl, ethyl, propyl, butyl, phenyl, p-methoxyphenyl, p-nitrophenyl or benzyl.

5. The protected cysteine of claim 1, wherein X and Y are independently of each other oxygen or nitrogen or wherein X is nitrogen and Y is oxygen.

6. The protected cysteine of claim 1, wherein n is an integer between 1 and 4, inclusive.

7. The protected cysteine of claim 1, wherein $R_3$ and $R_4$ are independently each other hydrogen, alkyl, allyl, tert-Butyloxycarbonyl (Boc), fluorenylmethyloxycarbonyl (Fmoc), tert-butyldimethylsilyl (TBS), methoxymethyl (MOM), ethoxymethyl (EOM), p-methoxybenzyl or p-nitrobenzyl or wherein $R_3$ is hydrogen or allyl and $R_4$ is Fmoc.

* * * * *